(12) United States Patent
Karpf et al.

(10) Patent No.: US 7,287,031 B1
(45) Date of Patent: Oct. 23, 2007

(54) COMPUTER SYSTEM AND METHOD FOR INCREASING PATIENTS COMPLIANCE TO MEDICAL CARE INSTRUCTIONS

(76) Inventors: Ronald Steven Karpf, 11425 Brandy Hall La., Gaithersburg, MD (US) 20878; Arthur Beau White, 9613 Barroll La., Kensington, MD (US) 20895

( * ) Notice: Subject to any disclaimer, the term of this patent is extended or adjusted under 35 U.S.C. 154(b) by 561 days.

(21) Appl. No.: 09/372,955

(22) Filed: Aug. 12, 1999

(51) Int. Cl.
 *G06F 17/00* (2006.01)
(52) U.S. Cl. .................. 707/100; 707/104.1; 705/2; 600/300
(58) Field of Classification Search .............. 705/1, 705/2, 3, 4; 600/300, 301; 715/536; 707/100, 707/104.1
See application file for complete search history.

(56) References Cited

U.S. PATENT DOCUMENTS

| | | | | |
|---|---|---|---|---|
| 5,827,180 | A | * | 10/1998 | Goodman ................. 600/300 |
| 5,842,175 | A | * | 11/1998 | Andros et al. ............. 705/3 |
| 5,867,821 | A | * | 2/1999 | Ballantyne et al. .......... 705/2 |
| 5,908,383 | A | * | 6/1999 | Brynjestad ................. 600/300 |
| 5,913,310 | A | * | 6/1999 | Brown ..................... 600/300 |
| 5,915,240 | A | * | 6/1999 | Karpf ...................... 705/2 |
| 5,933,136 | A |   | 8/1999 | Brown |
| 5,997,476 | A | * | 12/1999 | Brown ..................... 600/300 |
| 6,022,315 | A | * | 2/2000 | Iliff ........................ 600/300 |
| 6,032,119 | A | * | 2/2000 | Brown et al. ............... 705/2 |
| 6,623,529 | B1 | * | 9/2003 | Lakritz ..................... 715/536 |

OTHER PUBLICATIONS

Patient Compliance Statistics & References—Web Article.
Web Article—Failure of Patients to Follow Medical Recommendations Causes Host of Problems Each Year.
Web Article—The Multilevel Compliance Challenge Recommendations for a Call to Action.
Web Article—Medication Compliance: Therapy's Oldest Challenge.
Web Article 13 Compliance Interventions Yield Maximum Benefits.

(Continued)

*Primary Examiner*—Sam Rimell
(74) *Attorney, Agent, or Firm*—Dickstein Shapiro LLP

(57) ABSTRACT

The Electronic Compliance Promoter is a computer system for increasing a patient's compliance with medical post-care treatment instructions. The system permits the patient to review the treatment instructions that have been entered into a treatment instructions database by medical personnel at the time of the examination. The system includes a patient-client computer interface, a medical person-client interface, a treatment instructions database, and a compliance-server program. The database contains the post-visit care instructions and other types of information that the patient should have to understand and follow those instructions. The database also has treatment guideline information to assist the doctor in formulating the post-care treatment instructions. The patients client-computer interface provides a knowledge-based means for the patient to review interactively the Doctor's after care instructions, and measures compliance by tracking a patients' use of the specific designated diagnosis related resources. The medical personnel client-computer interface provides a knowledge-based means to designate the post-care medical visit instructions the patient is to follow. The compliance-server program tracks patients compliance and can send messages to patients reminding them to review the post-care treatment instructions. The Electronic Compliance Promoter system provides a means to significantly increase a patient's compliance with medical care instructions.

17 Claims, 34 Drawing Sheets

OTHER PUBLICATIONS

Web Article—Experts Call for "Shared Responsibility" in Health Care Among Patient, Provider & has/dul/HMO.

Web Article—You can Drag a Physicians to Guidelines . . . But You Can't Make Them Comply (Mostly).

Article: Few Adult Diabetic Patients Take Daily Aspirin Internal Medicare News: Sep. 3, 1999 p. 24.

Doctors Unsure About Patient Compliance—(Web Article).

* cited by examiner

Electronic Compliance Promoter
Patient Program

◇ Logon

Enter Username and Password

Username: [ ]

Password: [ ]

[ Submit ]   [ Reset ]

◇ Register/Update —650

| Prefix: | First Name: | MI: | Last Name: | Suffix: 660 |
|---|---|---|---|---|
| 601 | 602 | 603 | 604 | 605 |

Address: 606

| City: | State: | Zip: | Phone: |
|---|---|---|---|
| 607 | 608 | 609 | 610 |

| SSN: | Email: |
|---|---|
| 611 | 612 |

| Date of Birth | Sex: | Marital status: | Language: | Contact: |
|---|---|---|---|---|
| 613 | 614 | 615 | 616 | 617 |

| UserName: | Password: | Med-Password: |
|---|---|---|
| 618 | 619 | 620 |

631 — [ Submit ]   [ Reset ] — 632

[ Logoff ] — 640

Fig. 6

| | |
|---|---|
| 800 | Electronic Compliance Promoter |
| | Patient Program |

◇ Logon —— 805

◇ Register/Update —— 806

◇ Recent Physician Appointments —— 810                    813

| Dr. White - March 29, 1999       811 | ▲ |
|---|---|
| 812   Date: 3/29/1999   Physician: Dr. White | |
| Complaint: Dryness of mouth, excessive tiredness | |
| Diagnoses: Diabetes/Mellitus | |
| Dr. Karpf - April 2, 1999 —— 814 | ▼ |

◇ Treatment Instructions —— 815

| | Seq | Time | Description |
|---|---|---|---|
| 816 | 1 | 1 mo | Take insulin each day |
| | 2 | 3 mo | Blood sugar test and liver function at lab |
| | 3 | 3 mo | Return for consultation and followup with Dr. |

◇ Alerts —— 820

• Any faintness - contact Dr. immediately

◇ Followup —— 825

• Return for followup examination with Dr. after 3 mos

◇ Diagnosis Information —— 830

• Diabetes Mellitus:
• Coronary Heart Disease:

◇ Treatment Information —— 835

[ Logoff ] —— 840

Fig. 8

1000
Electronic Compliance Promoter
Medical Personnel Program - Data Entry ◇ Logon      1005

◇ Register/Update      1010

| Prefix: | First Name: | MI: | Last Name: | Suffix: |
|---|---|---|---|---|
| 1011 ▼ | 1012 | 1013 | 1014 | 1015 ▼ |

Degree:      Medical practitioner:   1039
| 1016 ▼ | 1017 ▼ |

Address: 1018

| City: | State: | Zip: | Phone: |
|---|---|---|---|
| 1019 | 1020 ▼ | 1021 | 1022 |

SSN:      Email:
| 1023 | 1024 |

UserName:      Password:
| 1025 | 1026 |

1031 — [ Submit ]      [ Reset ] — 1032

[ Logoff ] — 1090

Fig. 10

| 1200 | Electronic Compliance Promoter |
| --- | --- |
| | Medical Personnel Program - Data Entry |

◇ Logon —— 1205

◇ Register/Update —— 1210

◇ Identify Patient —— 1215

◇ Recent Physician Appointments —— 1220

Dr. White - January 1, 1999 —— 1221

Dr. Jones - February 1, 1999 —— 1230

◇ Office Visit

Date: 3/29/1999    Physician: Dr. White

1232    Complaint: Dryness of mouth, excessive tiredness —— 1250

Diagnoses: Diabetes/Mellitus —— 1235

1256    1257

1251 — ◇ Treatment instructions: ☐ Include ☐ Compliance Tracking

1252 — Diagnosis information: ☐ Include ☐ Compliance Tracking

1253 — Treatment information: ☐ Include ☐ Compliance Tracking

1254 — Followup..................: ☐ Include ☐ Compliance Tracking

1255 — Alerts......................: ☐ Include ☐ Compliance Tracking

Save —— 1290

Fig. 12

Electronic Compliance Promoter
Medical Personnel Program - Administration

1500

- Logon —— 1505
- Register/Update —— 1510
- Patient - Jane Doe —— 1520
  - Office visit - March 5, 1999 —— 1530
    - Diabetes/Mellitus —— 1540

|  | Accessed | Send reminder |
|---|---|---|
| 1550 — Treatment instructions: | ☐ 1541 | ☐ 1542 |
| 1555 — Diagnosis information: | ☐ | ☐ |
| 1560 — Treatment information: | ☐ | ☐ |
| 1565 — Alerts..................: | ☐ | ☐ |
| 1570 — Followup..................: | ☐ | ☐ |

- Office visit - July 2, 1999 —— 1531
    - Coronary Heart Disease

|  | Accessed | Send reminder |
|---|---|---|
| Treatment instructions: | ☐ | ☐ |
| Diagnosis information: | ☐ | ☐ |
| Treatment information: | ☐ | ☐ |
| Alerts..................: | ☐ | ☐ |
| Followup..................: | ☐ | ☐ |

[ Back ] —— 1580

[ Logoff ] —— 1590

| To: Ms. Jones 1610 |
| From: ECP 1620 |
| Subject: March 29, 1999 office visit 1630 |

Ms. Doe:

1640 Ref: Office visit with Dr. White on March 29, 1999

1650 Complaint: Dryness of mouth, excessive tiredness

Diagnosis: Diabetes/Mellitus

1660 Dr. White would like to remind you that a full understanding of Diabetes/Mellitus and the prescribed treatment will help you manage this disease. Please be sure to check disease and treatment information.

| State | Operation | Action |
|---|---|---|
| START (1801) | StartUp (1802) | • Startup Web Browser program and navigate to the URL of the Patient Program<br>• Display Patient Program screen<br>• State = WAIT_FOR_RESPONSE |
| WAIT_FOR_RESPONSE (1810) | Display web page (1811) | • Display the web page received from the server<br>• Set-focus to the 'Logoff' button<br>• State = WAIT_FOR_INPUT |
| WAIT_FOR_INPUT (1820) | Expand Collapse Section (1821) | • Set 'Selected-Section' = section selected by user<br>• If 'Selected section' section is in collapsed mode then<br>    Redisplay the screen with the 'Selected-section' section showing all data fields<br>Elseif 'Selected-Section' section is in expanded mode then<br>    Redisplay the screen with the 'Selected-Section' section in collapsed mode<br>End if<br>• State = WAIT_FOR_INPUT |
| | Reset (1822) | • If Reset button is for 'Logon section then<br>    Delete user data entry in Username and Password field of 'Logon' Section<br>Else if Reset button is for the 'SignUp/Update' section then<br>    Delete user data entry for the 'SignUp/Update' data fields<br>End if<br>• State = WAIT_FOR_RESPONSE |
| | Submit Logon (1823) | • Send a Logon message to the server with the user entered UserName and Password<br>• State = WAIT_FOR_RESPONSE |

Fig. 18B

| | |
|---|---|
| Submit SignUp Update (1824) | • Send a SignUp/Update message to the server with the patient registration information<br>• State = WAIT_FOR_RESPONSE |
| Submit Recent Appointment (1825) | • Send a get recent appointment message to the server with the appointment identifier<br>• State = WAIT_FOR_RESPONSE |
| Submit Logoff (1826) | • Send a Logoff message to the server<br>• State = WAIT_FOR_RESPONSE |
| Change Focus (1827) | • If user points-and-clicks with the mouse at a data entry field then<br>   Set-focus to the selected field<br>  End if<br>• State=WAIT_FOR_INPUT |
| Key-Entry (1828) | • For the data entry field that has the focus<br>   Add the Keyed entry to the value of the data entry field<br>• State = WAIT_FOR_INPUT |
| Display Diagnosis Info (1829) | • Open a new browser window<br>• Navigate to the URL of the Diagnosis information<br>• Display the Diagnosis information in the new browser window<br>• State = WAIT_FOR_INPUT |
| Display Treatment Info (1830) | • Open a new browser window<br>• Navigate to the URL of the Treatment Information<br>• Display the Treatment information in the new browser window<br>• State = WAIT_FOR_INPUT |

| State | Operation | Action |
|---|---|---|
| START (2001) | StartUp (2002) | • Startup Web Browser program and navigate to the URL of the MedPersonnel Data Entry Program<br>• Display Medpersonnel Data Entry Program screen<br>• State = WAIT_FOR_RESPONSE |
| WAIT_FOR_RESPONSE (2010) | Display web page (2011) | • Display the web page received from the server<br>• Set-focus to the 'Logoff' button<br>• State = WAIT_FOR_INPUT |
| WAIT_FOR_INPUT (2020) | Expand Collapse Section (2021) | • Set 'Selected-Section' = section selected by user<br>• If 'Selected section' section is in collapsed mode then<br>  Redisplay the screen with the 'Selected-section' section showing all data fields<br>Elseif 'Selected-Section' section is in expanded mode then<br>  Redisplay the screen with the 'Selected-Section' section in collapsed mode<br>End if<br>• State = WAIT_FOR_INPUT |
| | Reset (2022) | • If Reset button is for 'Logon' section then<br>  Delete user data entry in Username and Password field of 'Logon' Section<br>Else if Reset button is for the 'SignUp/Update' section then<br>  Delete user data entry for the 'SignUp/Update' data entry fields<br>Else if Reset button is for the 'Patient Logon' section then<br>  Delete user data entry for the 'Patient Logon' section<br>End if<br>• State = WAIT_FOR_INPUT |
| | Submit MedPersonnel Logon (2023) | • Send a Logon message to the server with the user entered UserName and Password of the MedPersonnel<br>• State = WAIT_FOR_RESPONSE |

Fig. 20B

| | |
|---|---|
| Submit Patient Logon (2024) | • Send a Logon message to the server with the user entered UserName and PIN of the Patient<br>• State = WAIT_FOR_RESPONSE |
| Submit SignUp Update (2025) | • Send a SignUp/Update message to the server with the MedPersonnel registration information<br>• State = WAIT_FOR_RESPONSE |
| Enter Diagnosis (2026) | • Select one or more entries from the Diagnosis Drop-down box<br>• State = WAIT_FOR_INPUT |
| Enter Include Treatment Information (2027) | • If the Include treatment type checkbox is checked then<br>    Uncheck the checkbox<br>Elseif the Include treatment type checkbox is not checked then<br>    Check the checkbox<br>End if<br>• State = WAIT_FOR_INPUT |
| Enter Track Treatment Information (2028) | • If the Tract treatment type checkbox is checked then<br>    Uncheck the checkbox<br>Elseif the Track treatment type checkbox is not checked<br>And the associated Include Treatment box is checked then<br>    Check the checkbox<br>End if<br>• State = WAIT_FOR_INPUT |
| Submit Logoff (2029) | • Send a Logoff message to the server<br>• State = WAIT_FOR_RESPONSE |

Fig. 20C

| | |
|---|---|
| Change Focus (2030) | • If user points-and-clicks with the mouse at a data entry field then<br>　　Set-focus to the selected field<br>　End if<br>• State = WAIT_FOR_INPUT |
| Key-Entry (2031) | • For the data entry field that has the focus<br>　　Add the Keyed entry to the value of the data entry field<br>• State = WAIT_FOR_INPUT |
| Display Recent Appointment (2032) | • Open a new browser window<br>• Navigate to the URL of the Recent Appointment information<br>• Display the Diagnosis information in the new browser window<br>• State = WAIT_FOR_INPUT |
| Save (2033) | • Send a Save message to the server<br>• State = WAIT_FOR_RESPONSE |
| Enter Treatment Instructions (2034) | • Edit the treatment instruction in the popup dialog box<br>• Set value of TreatmentEdit html (hidden) field to True<br>• State = WAIT_FOR_INPUT |

| State | Operation | Action |
|---|---|---|
| START (2201) | StartUp (2202) | • Startup Web Browser program and navigate to the URL of the MedPersonnel Administration Program<br>• Display Patient Program screen<br>• State = WAIT_FOR_RESPONSE |
| WAIT_FOR_RESPONSE (2210) | Display web page (2211) | • Display the web page received from the server<br>• Set-focus to the 'Logoff' button<br>• State = WAIT_FOR_INPUT |
| WAIT_FOR_INPUT (2220) | Expand Collapse Section (2221) | • Set 'Selected-Section' = section selected by user<br>• If 'Selected section' section is in collapsed mode then<br>   Redisplay the screen with the 'Selected-section' section showing all data fields<br>Elseif 'Selected-Section' section is in expanded mode then<br>   Redisplay the screen with the 'Selected-Section' section in collapsed mode<br>End if<br>• State = WAIT_FOR_INPUT |
| | Reset (2222) | • If Reset button is for 'Logon' section then<br>   Delete user data entry in Username and Password field of 'Logon' Section<br>Else if Reset button is for the 'SignUp/Update' section then<br>   Delete user data entry for the 'ignUp/ data entry fields<br>End if<br>• State = WAIT_FOR_INPUT |
| | Submit Logon (2223) | • Send a Logon message to the server with the user entered UserName and Password<br>• State = WAIT_FOR_RESPONSE |
| | Submit SignUp Update (2224) | • Send a SignUp/Update message to the server with the MedPersonnel registration information<br>• State = WAIT_FOR_RESPONSE |

Fig. 22B

| | |
|---|---|
| Submit Logoff (2225) | • Send a Logoff message to the server<br>• State = WAIT_FOR_RESPONSE |
| Change Focus (2226) | • If user points-and-clicks with the mouse at a data entry field then<br>　Set-focus to the selected field<br>End if<br>• State = WAIT_FOR_INPUT |
| KeyEntry (2227) | • For the data entry field that has the focus<br>　Add the Keyed entry to the value of the data entry field<br>• State = WAIT_FOR_INPUT |
| Display Office Visit (2228) | • Send a Get Office Visit Info to the server with the Patient Identifier<br>• State = WAIT_FOR_RESPONSE |
| Back Button (2229) | • Send a Get All Patients message to the server<br>• State = WAIT_FOR_RESPONSE |

| State | Operation | Action |
|---|---|---|
| START (2410) | StartUp (2411) | • Startup Treatment instructions database program<br>• If open Treatment Instructions Database fails then<br>    MsgOperator "Database cannot be opened"<br>    State=END<br>  Else<br>    State=WAIT_FOR_REQ<br>  End if |
| WAIT_FOR_REQ (2420) | ParseRequest (2421) | • If Request is to Logoff then<br>    State=LOGOFF<br>  else if Request is to process Request-msg then<br>    If Request-msg is from Patient Program then<br>        State=PATIENT_RESPONSE<br>    Elseif Request-msg is from Medical Personnel Data Entry program then<br>        State=MEDPERSONNEL DATA ENTRY<br>    Elseif Request-msg is from Medical Personnel Administration program<br>        then State=MEDPERSONNEL ADMINISTRATION<br>    Elseif Request-msg is to Calculate compliance and send reminders then<br>        State=AUTO_CALC COMPLIANCE<br>    End if<br>  End if |
| PATIENT_RESPONSE (2430) | Msg=Start (2431) | • Generate a Patient Response page with Patient Logon and Register/Update sections<br>• Send Page to client<br>• State = WAIT_FOR_REQ |

Fig. 24B

| | |
|---|---|
| Msg=Logon (2432) | • Parse the UserName and Password information from the QueryString<br>• If the UserName and Password are in the Patients database table then<br>  -the user is validated and generate a web page with Patient Logon, Register/Update sections (filled in with the Patients current information) and Recent Appointments sections<br>  -Insert a record into the LoginLog table 315 recording the login<br>  Else<br>    Generate a Patient Response page with Patient Logon and Register/Update sections<br>  End if<br>• Send page to client<br>• State = WAIT_FOR_REQ |
| Msg=SignUp (2433) | • Parse the SignUp fields from the QueryString<br>• Insert the SignUp data into the Patients database table<br>• Logon the user by generating a web page with Patient Logon, Register/Update sections (filled in with the Patients current information) and Recent Appointments sections<br>• Insert a record into the LoginLog table 315 recording the login<br>• Send page to client<br>• State=WAIT_FOR_REQ |
| Msg=Update (2434) | • Parse the Update fields from the QueryString<br>• Update the data in the Patients database table with the new information<br>• Generate a web page with Patient Logon, Register/Update sections (filled in with the Patients current information) and Recent Appointments sections<br>• Send page to client<br>• State= WAIT_FOR_REQ |

Fig. 24C

| | Msg=Recent Appointment (2435) | • Parse the PatientID and unique identifier for the recent appointment from the QueryString<br>• Generate a web page with the Patient Logon, Register/Update, Recent Physician Appointments and for the recent appointment the Treatment Instructions, Alerts, FollowUp, Diagnosis and Treatment Information sections<br>• Update the PatCompliance table to show that the patient has accessed the compliance information for this appointment on today's data<br>• Send page to client<br>• State=WAIT_FOR_REQ |
|---|---|---|
| | Msg=Logoff (2436) | • Generate a Patient Response page with Patient Logon and Register/Update sections<br>• Send Page to client<br>• State=WAIT_FOR_REQ |
| MEDPERSONNEL DATA_ENTRY (2440) | Msg= Start (2441) | • Generate MedPersonnel Data Entry page with Logon and Register/Update sections<br>• Send Page to client<br>• State=WAIT_FOR_REQ |
| | Msg=MedPers Logon (2442) | • Parse the UserName and Password information from the QueryString<br>• If the UserName and Password are in the MedPersonnel database table then<br>  -The user is validated and generate a web page with Logon, Register/Update sections (filled in with the Medical Personnel's current information) and Identify Patients sections<br>  -Insert a record into the LoginLog table 315 recording the login<br> Else<br>  -Generate MedPersonnel Data Entry page with Logon and Register/Update sections<br> End if<br>• Send page to client<br>• State=WAIT_FOR_REQ |

Fig. 24D

| | |
|---|---|
| Msg=SignUp (2443) | • Parse the SignUp fields from the QueryString<br>• Insert the SignUp data into the Medpersonnel database table<br>• Logon the user by generating a web page with Logon, Register/Update sections filled in with the Medical Personnel's current information) and Identify Patient sections<br>• Insert a record into the LoginLog table 315 recording the login<br>• Send page to client<br>• State=WAIT_FOR_REQ |
| Msg=Update (2444) | • Parse the Update fields from the QueryString<br>• Update the data in the MedPersonnel database table with the new information<br>• Generate a web page with Logon, Register/Update sections (filled in with the Patients current information) and Identify Patient sections<br>• Send page to client<br>• State=WAIT_FOR_REQ |
| Msg=Patient Logon (2445) | • Parse the UserName and Password information from the QueryString<br>• If the Username and Password are in the Patients database table then<br>  -The patient is validated and generate a web page with Patient Logon, Register/Update sections (filled in with the Patients current information), Identify Patient, and Recent Physician Appointments sections<br>Else<br>  Generate a web page with Logon, Register/Update sections (filled in with the Patients current information) and Identify Patient sections<br>End if<br>• Send page to client<br>• State=WAIT_FOR_REQ |

Fig. 24E

| | | |
|---|---|---|
| | Msg=Back (2446) | • Parse the QueryString for all input including appointment, information, complaint, diagnoses, and treatment instructions<br>• For each diagnosis, if the Include field is set to true then insert into the PatCompliance table the treatment instructions information. If the Recommended field is false then insert the text of the practitioners edited treatment instructions into the ClinGuideLine table<br>• Generate MedPersonnel Data Entry page with Logon and Register/Update (filled in with the Patients current information), Identify Patient sections<br>• State=WAIT_FOR_REQ |
| | Msg=Logoff (2447) | • Generate a MedPersonnel Data Entry page with Logon and Register/Update sections<br>• Send page to client<br>• State=WAIT_FOR_REQ |
| MEDPERSONNEL ADMINISTRATION (2450) | Msg=Start (2451) | • Generate MedPersonnel Administration page with Logon and Register/Update sections<br>• Send Page to client<br>• State=WAIT_FOR_REQ |
| | Msg= Logon (2452) | • Parse the UserName and Password information from the QueryString<br>• If the UserName and Password are in the MedPersonnel database table then<br>  -The user is validated and generate a web page with Logon, Register/Update, and Patients sections, and for each patient, subsections with each office visit for that patient Insert a record into the LoginLog table 315 recording the login<br>Else<br>  -Generate MedPersonnel Administration page with Logon and Register/Update sections<br>End if<br>• Send page to client<br>State=WAIT_FOR_REQ |

Fig. 24F

| | |
|---|---|
| Msg= SignUp (2453) | • Parse the SignUp fields from the QueryString<br>• Insert the SignUp data into the MedPersonnel database table<br>• Logon the user by generating a web page with Logon, Register/Update, and Patients sections, and for each patient, subsections with each office visit for that patient<br>• Insert a record into the LoginLog table 315 recording the login<br>• Send page to client<br>• State=WAIT_FOR_REQ |
| Msg= Update (2454) | • Parse the Update fields from the QueryString<br>• Update the data in the MedPersonnel database table with the new information<br>• Generate a web page with Logon, Register/Update, and Patients sections, and for each patient, subsections with each office visit for that patient<br>• Send page to client<br>• State=WAIT_FOR_REQ |
| Msg= Get Office Visit (2455) | • Parse the PatientID from the QueryString<br>• Generate a web page with Logon, Register/Update, and a section for the selected Patient. The patient will have subsections for each office visit. Each subsection will in turn have subsections for each of the diagnoses,<br>• Send page to client<br>• State=WAIT_FOR_REQ |
| Msg= Back (2456) | • Parse the QueryString for any requests by the Medical Personnel to send a non-compliance reminder to the patient about their treatment instructions. Send the reminder according to the patients preferred means of contact.<br>• Generate a web page with Logon, Register/Update, and Patients sections, and for each patient, subsections with each office visit for that patient<br>• Send page to client<br>• State=WAIT_FOR_REQ |

Fig. 24G

| | | |
|---|---|---|
| | Msg= Logoff (2457) | • Generate a MedPersonnel Administration page with Logon and Register/Update sections<br>• Send Page to client<br>• State=WAIT_FOR_REQ |
| AUTO_CALC_COMPLIANCE (2460) | Execute compliance calculation and reminders program (2461) | 1. For each appointment that is more than 1 week old and for Each Patient in the database, and only for those treatment instructions with the TrackIt flag set to 'True', calculate and update the MeasCompliance in the MedEncounter database table.<br>2. For each Patient in the database, and only for those treatment instructions with the TrackIt flag set to 'true', calculate and update the MeasCompliance in the Patients database table<br>3. For every Patient in the database that is non-compliant send a reminder message, according to the patient's preferred means of contact.<br><br>• When processing of the above steps is completed State = WAIT_FOR_REQ |
| LOGOFF (2470) | CloseDB (2471) | • Close the Treatment Instructions Database<br>• State=END |
| END (2480) | Stop Server (2481) | • Terminate execution of the Treatment instructions database program |

COMPUTER SYSTEM AND METHOD FOR INCREASING PATIENTS COMPLIANCE TO MEDICAL CARE INSTRUCTIONS

FIELD OF THE INVENTION

This invention relates to a computer system and method for providing patients with access to the information they need to understand and follow the post-visit medical care instructions that arise from a visit with a medical practitioner.

BACKGROUND OF THE INVENTION

There is a significant problem with patients' failing to follow a medical practitioners post-examination treatment instructions. The terminology we use for this is compliance. While the patient may choose to consciously ignore medically necessary advice, the greater problem is with patients who leave the medical practitioners office without being sufficiently cognizant of the diagnosis or prepared to follow the recommended therapeutic intervention. This long recognized problem has been intractable, defying easy solution, but which can now be addressed due to advances in telecommunications and computer technology. An associated problem is that health care practitioners often fail to comply with existing ever-changing treatment guidelines.

Our awareness of the problem arises in part from experience with Diabetes. Diabetes Mellitus is the fourth leading cause of death in the United States and a major cause of blindness and heart disease. It is the major cause of blindness in person's 24-74 years of age, with 39,000 new cases each year. Ten percent of patients with diabetes develop renal disease. Patients with Type-2 diabetes have a 28-fold increased risk of limb amputation, and approximately 50% of people with diabetes for 25 years have evidence of neuropathy. Diabetes imposes a 2 to 4-fold lifetime risk of heart disease, and a 5-fold lifetime risk of a stroke.

Often, even physicians do not comply with the American Diabetes Association (ADA) standards of practice. The ADA publishes standards of practice for comprehensive care of Type-2 Diabetes Mellitus (DM), including guidelines for optimizing glycemic control. It is well documented that physicians and other health care providers often do not comply with the existing ADA guidelines. And even when the health care provider strictly adheres to the recommended disease specific intervention, the patient is likely to depart from the recommended therapy either through neglect or misunderstanding. There is a clear need for a system that will assist both the patient and health care practitioner adhere to recommended therapeutic guidelines. We believe that the proposed system will enhance the treatment process and outcome of disease management for diabetic patients and patients with other diseases.

Patients may fail to accurately follow doctor's order for a variety of reasons. All to often they leave the medical encounter without a clear understanding of the diagnosis or recommended course of action. Being ill is traumatic—and under the pressures of a medical examination, patients are often unable to focus on the instructions for treatment. They may have difficulty understanding the medical terminology. There is a cognitive difficulty in remembering instructions for complicated regimens. The age of the patient or the national origin of the patient or doctor may be a factor. Older patients may simply have hearing problems. As simple a distraction as children in the examination room or a loud air conditioner may make verbal communications difficult.

For whatever reason, the ability of patients to leave a medical encounter fully cognizant of the information they need to continue care is a real problem with serious medical consequences. The purpose of this system is to significantly assist patients in their compliance to the post-visit medical care instructions that arise from a visit to a doctor.

The current means to address the problem primarily rely on pamphlets and/or packets of printed information appropriate to the patient's complaint that is used to supplement the practitioner's verbal instructions. For instance, lower back pain is a common complaint, and doctors will often provide patients with a booklet describing the problem and the appropriate exercise treatments.

While this has been helpful the approach has serious problems. The information can only be maintained on a limited number of the most common complaints, and may not be in the native language of the patient. Supplies of pamphlets may run out, and more recent medical advances and treatment guidelines may easily outdate the information. HMO's and large managed care practices are beginning to issue medical information books to members that explain the diagnosis, treatment and prognosis for the most common ailments. Unlike pamphlets provided to the patient during a medical visit and addressing the specific patient complaint, these books are entirely general, and may easily become out-of-date, and may be lost or otherwise unavailable to the patient. Another problem with this approach is that it only provides general information that is meant to supplement the practitioners instructions, but does nothing to assist the patient with the specific instructions deemed appropriate to their situation.

SUMMARY OF THE INVENTION

The main object of the present invention is a computer system that assists patients to follow or comply with the post-examination medical treatment that they are to follow. A key feature of the invention is that the medical personnel may enter into a treatment instructions database, at the time of the examination, the precise treatment instructions that the doctor issues to the patient. Since the treatment instructions database is accessible to the patient, they may at any time subsequent to the examination, review the exact instructions that have been provided to them by the medical practitioner.

Treatment instructions include both the therapeutic regimen as well as information about the disease and treatment, since a patient who understands the disease and treatment is more likely to be compliant. To aid the medical practitioner to enter the therapeutic regimen, source materials are provided. The most current recommended diagnosis specific treatment guidelines are provided as a starting point in specifying the treatment instructions. The medical practitioner is not restricted to the use of the available treatment guidelines but may modify them in part or full. Other types of treatment instructions include disease and treatment information, alerts and recommended followup. The system also allows the medical practitioner to specify which types of treatment instructions information to include or exclude. We do not want to overburden patient's with too much information as this may confuse or otherwise cause them to avoid using the system.

Treatment guidelines change frequently to reflect new research and medications, and it is difficult for the health care practitioner to maintain a comprehensive up-to-date knowledge of the latest treatment guidelines. Often more specificity may be added to treatment guidelines to distinguish the treatment preference for patients depending on age, sex, and ethnicity. An important feature of the system is that since the treatment guidelines are accessed over a network, the medical practitioner will always be prompted with the most up-to-date treatment guidelines from the source site.

Another key feature of the system is that the treatment instructions are available to patients upon demand. Since the instructions have been entered into a database, patients may access the database from a computer through a patient program user-interface, and review the treatment information for any prior medical examination. A key factor in patient compliance is an understanding of the therapeutic regimen, as well as an understanding of the diagnosis and treatment. The system provides full and clear treatment instructions in a standard format, and information sources that fully explain the diagnosis and the recommended treatment. Items of special importance, termed in this invention 'alerts' and 'followup' are presented in separate sections to highlight their importance, to the patient. Alerts are items of information of special importance, such as possible medication side effects or symptoms that the patient should be aware that if they occur, immediate medical attention is required. Followup refers to future follow-up medical examination.

To maximize the usability of the system by patients, we make every attempt to present the information to patients in a manner that is easy for them to access. Towards this end, the system allows the user to specify preferences.

The patient may specify a language preference. Since much of the information that is presented is from suggested treatment guidelines and up-to-date information sources, this information can be presented in a language of their choice. Patients may also specify the mechanism by which they will receive compliance reminder messages. A compliance reminder message is sent to a patient who has not accessed the treatment information. The mechanism for this can be Email, phone, regular mail, or beeper.

Another key feature of the system is to remind patients to comply with the treatment instructions. This is accomplished by tracking the patients access to treatment information and using it to generate a patient's measure of compliance.

If a patient has not accessed any of the specified treatment information they are termed non-compliant and they are sent a reminder message to check the prescribed information sources. If a patient has accessed some, but not all of the specified treatment information they are termed partially compliant and they are send a reminder message to review the information they have not yet accessed. If a patient has accessed all the specified treatment information for a medical encounter, then they are termed fully compliant and no reminder messages are sent.

Having a measurable index of patient compliance and a means to take action based on patient lack of full compliance is one of the key elements of this invention and a primary means to increase a patients compliance to medical care instructions.

Another important feature of the system is the ease with which complex treatment protocols are presented to the patient. A standard format is utilized, and complex treatment instructions that require multiple actions followed in a sequence of steps which may be time dependent, are presented to the patient in a linear fashion explicitly showing the relationship between the sequence of steps they must follow.

Another important object of the invention is the wide availability of the system. The patient may access all treatment instructions for all medical examinations from any computer that has a network connection to the Internet.

An additional feature is that all these treatment instructions are now administered in a similar way, so once the user can successfully understand how to review treatment instructions for any single examination, they understand the means to review the treatment instructions for any examination. This familiarity will reinforce the patient's use of the system and foster better patient compliance.

Other objects and advantages of the invention will be set forth in part in the description that follows and in part will be obvious from the description or may be learned by practice of the invention. The objects and advantages of the invention will be realized and attained by means of the elements and combinations particularly pointed out in the appended claims.

BRIEF DESCRIPTION OF THE DRAWINGS

The accompanying drawings, which are incorporated in and constitute a part of the specification, illustrate the preferred embodiment of the invention, and together with the detailed description of the preferred embodiment, serve to explain the principles of the invention.

FIG. 6 is an example of the user-interface logon screen of the patient program with all sections of the user-interface expanded.

FIG. 8 is an example of the user-interface screen of the patient program showing the treatment instructions for a selected office visit.

FIG. 10 is an example of the user-interface screen of the medical personnel data entry program showing the medical personnel registration section.

FIG. 12 is an example of the user-interface of the medical personnel data entry program used to enter the patient diagnosis and treatment instructions.

FIG. 15 is an example of the user-interface of the medical personnel administration program showing status of the treatment instructions for a patient visit.

FIG. 16 is an example of a compliance reminder message sent via Email to a patient.

FIG. 18 is a state table describing the operation of the patient program.

FIG. 20 is a state table describing the operation of the medical personnel data entry program.

FIG. 22 is a state table describing the operation of the medical personnel administration program.

FIG. 24 is a state table describing the operation of the treatment instructions server program.

DETAILED DESCRIPTION OF THE PREFERRED EMBODIMENT

References will now be made in detail to the preferred embodiments of the invention, examples of which are illustrated in the accompanying drawings. Wherever possible, the same reference numbers will be used throughout the drawings to refer to the same or like parts.

1. An Electronic Compliance Promoter

A. Hardware, Operating System and Application Development Software

Figure 1:
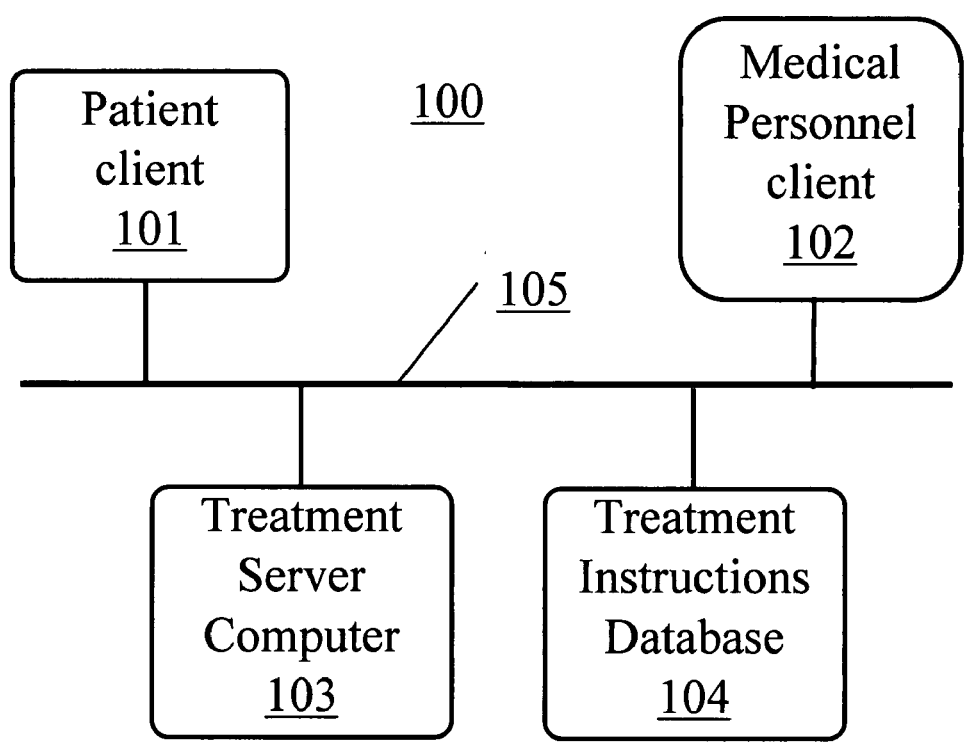
FIG. 1 is a block diagram of the invention.

FIG. 1 is a block diagram of the preferred embodiment of the present invention. A system 100 of FIG. 1 illustrates the patient-client computer 101, the medical personnel-client computer 102, the treatment server computer 103, the treatment instructions database 104, and the network interface 105 over which they establish a connection and communicate. In the preferred embodiment the network interface protocol that is used is the industry standard network protocol TCP/IP.

Figure 2:
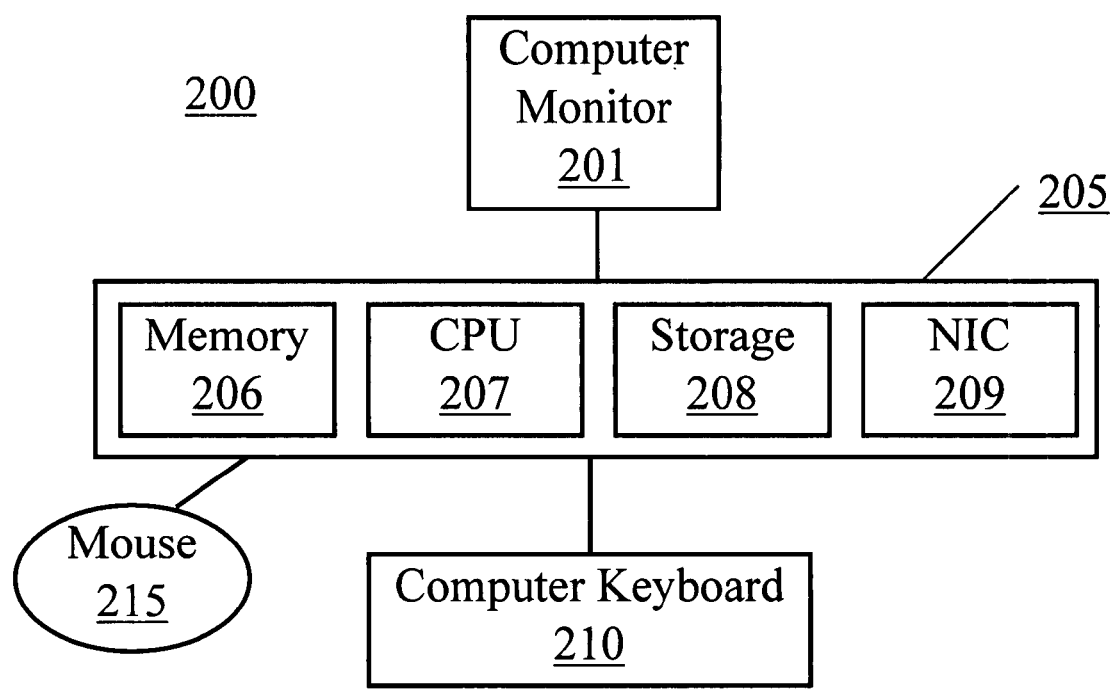
FIG. 2 is a block diagram of the computers used in the system.

FIG. 2 is a block diagram of the computers used in the system. In the preferred embodiment the same computer hardware was used for the patient-client computer 101, the medical personnel-client computer 102, and the treatment server computer 103.

In the preferred embodiment, the system 200 consists of a computer monitor 201, computer 205, computer mouse 215, and a computer keyboard 210. The computer 205 includes a memory 206 and a processor (CPU) 207, a mass storage device 208, and a network interface card (NIC) 209. Monitor 201, the computer mouse 215, and computer keyboard 210, are connected to computer 205 in a manner known to persons of ordinary skill in the art.

Computer 205 preferably is a Compaq Presario 5280, the keyboard 210 is a Compaq Easy Access Internet Keyboard, and both manufactured by the Compaq Corporation. The monitor 201 is an Acer 77 manufactured by the Acer Peripherals America Incorporated of San Jose, Calif. The NIC 209, is a Linksys Ether16 Lan Card, 16-bit ISA Ethernet Adapter card manufactured by the Linksys Corporation of Irvine, Calif. The computer mouse 215 is a Compaq Corporation 2-button Mouse, manufactured by the Compaq Corporation. The computer network uses a Linksys 5-port workgroup hub manufactured by the Linksys Corporation of Irvine, Calif. The computers are connected to the Linksys 5-port workgroup hub using 10BaseT cable in a manner known to persons of ordinary skill in the art.

In the preferred embodiment, the patient-client computer 102 and the medical personnel-client computer 103 are executing under Microsoft Windows 98. The client programs run under the Microsoft Internet Explorer Browser 4.0 manufactured by the Microsoft Corporation of Redmond, Calif., and are written in the industry standard hypertext markup language (HTML).

In the preferred embodiment, the treatment instructions server computer 103 is executing under Microsoft Windows NT Server 4.0, and is running the Microsoft Internet Information Server 4.0. The treatment instructions database program is written in the Active Server Page (ASP) language, version 2.0 using Visual Basic Script, and utilizes the ActiveX Data Objects (ADO) data access component to communicate with the database using the Microsoft Access ODBC driver. The treatment instructions database is a Microsoft Access 97 database. The Microsoft Corporation of Redmond, Wash. manufactures the six above-mentioned products. Other embodiments may use other hardware and software components.

B. Data Structures

Figure 3:
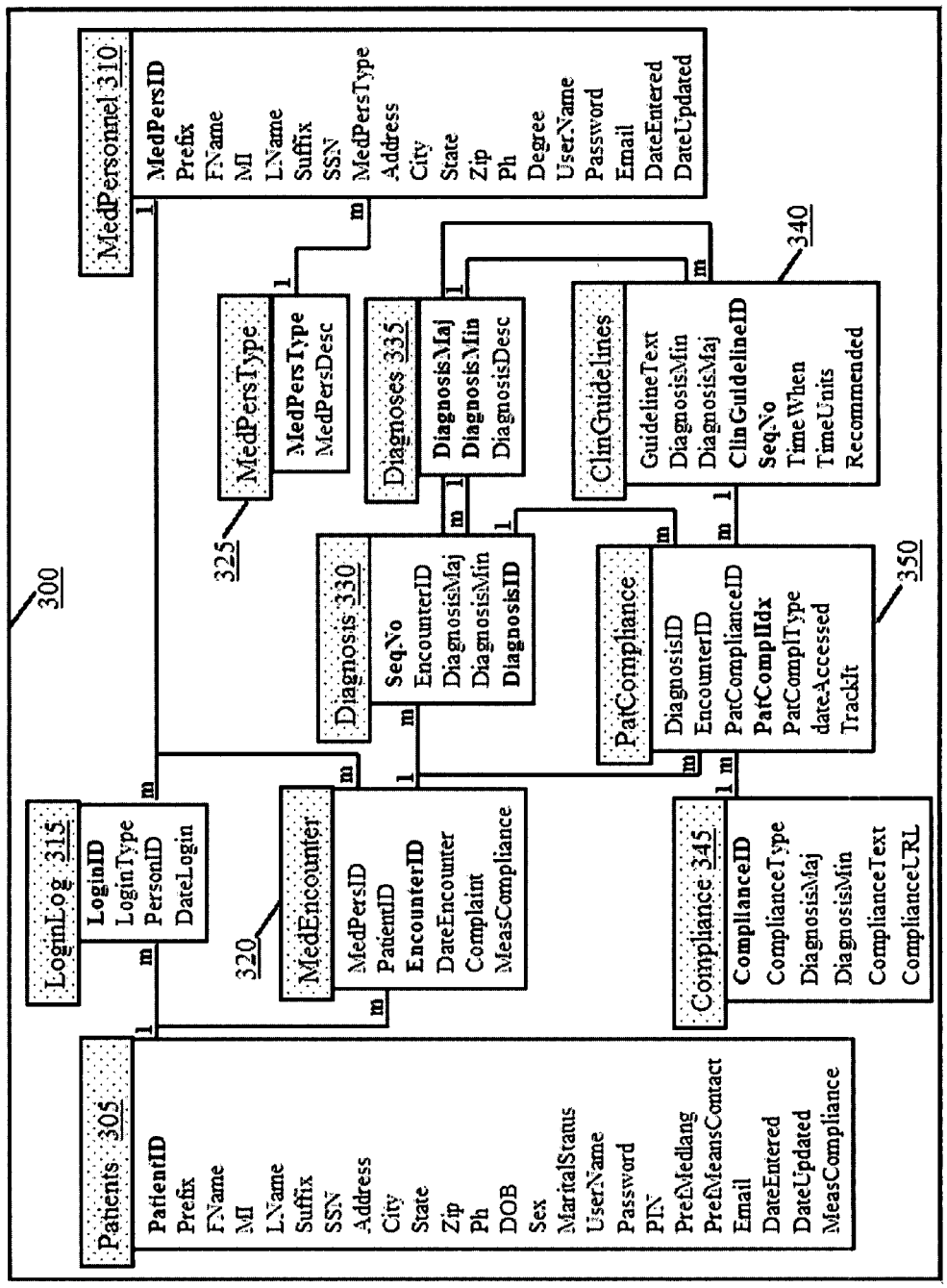
FIG. 3 is an entity-relationship diagram of the treatment instructions database.

FIG. 3 shows an entity-relationship or ER diagram 300 of the treatment instruction database. It shows the 10 relational tables that comprise the treatment instructions database, the fields of each table, the primary key of each table and the primary-foreign key relationship between fields of different tables. The discussion below also provides the attributes of each field of every table. On the figure, the primary key field is highlighted in bold print. Relationship lines drawn between the tables identify primary-foreign key relationships between the tables. The label '1' and 'm' on either side of the relationship line indicates that tables have a one-to-many relationship, with many records on the 'm' associated table possibly existing for each unique row of the '1' associated table.

Table 'Patients' 305 contains a single record with information about every patient that is registered to use the system. The primary key, 'PatientID', is a unique long integer generated by Microsoft Access using the counter attribute. The other fields of table 'Patients' 305 include the patients name stored in the fields 'Prefix' a text field of length 8 with the title of a patient such as 'Mr.' or 'Mrs.'; 'FName' a text field of length 24 with the first name of the patient; 'MI' a text field of length 1 with the middle initial of the patient; 'LName' a text field of length 24 with the last name of the patient; and 'Suffix' a text field of length 8 with a name suffix such as 'Ph.D', or 'MD'. Still other fields of table 'Patients' 305 include patient identifiers stored in the fields 'SSN' a text field of length 11 with the social security number of the patient; 'DOB' a date field with the date of birth of the patient; 'Sex' a text field of length one with either 'M' or 'F' for 'Male' or 'Female'; 'MaritalStatus' a field of length 1 with the marital status of the patient coded as 'S', 'M', 'D', or 'W' for 'Single', 'Married', 'Divorced', or 'Widowed' respectively. Other fields of table 'Patients' 305 store the address of the patient in fields 'Address' a text field of length 50 with the address of the patient; 'City' a text field of length 24 with the home city of the patient; 'State' a text field of length 2 with the 2 character postal abbreviation of the home state of the patient; 'Zip' a text field of length 10 with the postal zip code of the patient, and 'Ph' a text field of length 12 with the area code and phone number of the patient. Other fields of table 'Patients' 305 store the Username and Password of the patient in fields 'Username' a text field of length 24 with the Username of the patient; 'Password' a text field of length 24 with the Password of the patient, and 'PIN' a text field of length 24 with the patient's Password that is used by medical personnel to identify the patient for data entry of the treatment instructions. The remaining fields of table 'Patients' 305 are 'PrefMedLang' a text field of length 8 used to store the patients language preference for reviewing treatment instructions; 'PrefMeansContact' a text field of length 8 used to store the means by which a patient prefers to receive reminder compliance messages; 'DateEntered' a date field with a date and time stamp for when the patient registered with the system; 'DateUpdated' field with the date attribute with a date and time stamp for when the patient last updated the registration information, 'Email' a text field of length 124 with the Email address of the patient, and 'MeasCompliance a text field of length 24 with the patient's overall measure of compliance. When the patient first registers the 'DateEntered' and 'DateUpdated' are set to the same value.

Table 'MedPersonnel' 310 contains a single record with information about every medical practitioner that is registered to use the system. The primary key, 'MedPersID', is a unique long integer generated by Microsoft Access using the counter attribute. The other fields of table 'MedPersonnel' 310 include the name stored in the fields 'Prefix' a text field of length 8 with the title of a patient such as 'Dr.' or 'Mr'; 'FName' a text field of length 24 with the first name of the medical personnel; 'MI' a text field of length '1' with the middle initial of the medical personnel; 'LName' a text field of length 24 with the last name of the medical personnel; and 'Suffix' a text field of length 8 with a name suffix such as 'Ph.D', or 'MD'. A social security number identifier for the medical personnel is stored in field 'SSN' a text field of length 11, and their educational level of attainment or educational degree is stored in the field 'Degree' a text field of length 8. The field 'MedPersType' of table 'MedPersonnel' 310 has a many-to-one primary-foreign key relationship with the field 'MedPersType' of table 'MedPersType' 325 and has the same attributes. Medical personnel logon validation are stored in fields 'Username' a text field of length 24 with the Username of the medical personnel, and 'Password' a text field of length 24 with the Password of the medical personnel. The remaining fields of table 'MedPersonnel' 310 are 'DateEntered' a date field with a date and time stamp for when the medical personnel registered with the system; 'DateUpdated' field with the date attribute with a date and time stamp for when the medical personnel last updated the registration information, and 'Email' a text field of length 124 with the Email address of the medical personnel. Other fields of table 'MedPersonnel' 310 store the address of the patient in fields 'Address' a text field of length 50 with the work address of the medical personnel; 'City' a text field of length 24 with the work city of the medical personnel; 'State' a text field of length 2 with the 2 character postal abbreviation of the work state of the medical personnel; 'Zip' a text field of length 10 with the postal zip code of the medical personnel, and 'Ph' a text field of length 12 with the area code and phone number of the medical personnel.

Table 'LoginLog' 315 contains information that is a log of all users that successfully access the system with a valid Username and Password. The primary key, 'LoginID' is a unique long integer generated by Microsoft Access using the counter attribute. The other fields of table 'LoginLog' 315 include 'LoginType', a field of length 8 with an encoding of the category of person who has successfully logged onto the system, and its valid entries are 'patient' for a patient using the patient program to view their treatment instructions, 'medpers' for medical personnel using the medical personnel data entry program, and 'admin' for medical personnel using the medical personnel administration program. The field 'DateLogin' is a date field with the date and time that the user logged onto the system. If the value of the field 'LoginType' is 'patient' then the field 'PersonID' of table 'LoginLog' 315 has a many-to-one primary-foreign key relationship with the field 'PatientID' of table 'Patients' 305 and has the same attributes. If the value of the field 'LoginType' is 'medpers' or 'admin' then the field 'PersonID' of table 'LoginLog' 315 has a many-to-one primary-foreign key relationship with the field 'MedPersID' of table 'MedPersonnel' 310 and has the same attributes.

Table 'MedEncounter' 320 contains a single record with information about every medical encounter or office visit between a patient and a medical practitioner. The primary key, 'EncounterID', is a unique long integer generated by Microsoft Access using the counter attribute. The field 'MedPersID' of table 'MedEncounter' 320 has a many-to-one primary-foreign key relationship with the field 'MedPersID' of table 'MedPersonnel' 310 and has the same attributes. The field 'PatientID' of table 'MedEncounter' 320 has a many-to-one primary-foreign key relationship with the field 'PatientID' of table 'Patients' 305 and has the same attributes. The other fields of this table include 'DateEncounter' which has a date attribute and contains the date of the medical encounter; 'Complaint' a text field of length 255 with the patients complaint or reason for the medical appointment, and 'MeasCompliance' a text field of length 24 with the system calculated patient measure of compliance for the associated medical visit.

Table 'MedPersType' 325 is a lookup table that has a single record for every category of medical personnel describing the type of medical personnel. The primary key 'MedPersType', is an integer field and is a numeric coding of a unique type of medical personnel. The field 'MedPersDesc' is a text field of length 50 that has a description of the type of medical personnel corresponding to the value in the primary key field 'MedPersType'. For instance, the record with a value of '1' for 'MedPersType' has a corresponding record value of 'Dr.' for the 'MedPersDesc' field.

Table 'Diagnosis' 330 contains information about the diagnosis by a medical practitioner of the patients complaint or reason for the office visit. The field 'DiagnosisID' is a unique long integer generated by Microsoft Access using the counter attribute. The primary key is the composite index formed by 'DiagnosisID' and 'SeqNo'. The field 'EncounterID' of table 'Diagnosis' 330 has a many-to-one primary-foreign key relationship with the field 'EncounterID' of table 'MedEncounter' 320 and has the same attributes. Any medical encounter can result in several different diagnoses so there may be several records in this table for a single patient medical encounter distinguished by a SeqNo starting with '1' and incrementing by '1'. The combination of field 'DiaignosisID' and 'SeqNo' provides a unique identifier for an individual diagnosis. The fields 'DiagnosisMaj' and 'DiagnosisMin' of table 'Diagnosis' 330 have a many-to-one primary-foreign key relationship with the fields 'DiagnosisMaj' and 'DiagnosisMin' of table 'Diagnoses' 335 and have the same attributes.

Table 'Diagnoses' 335 contains information categorizing different diagnoses. Each diagnosis has a major and minor category coding. For instance Diabetes would be a major diagnoses category and each of the different types of Diabetes would be coded in the minor category coding. The primary key for this table is a composite index of two fields 'DiagnosisMaj' and 'DiagnosisMin' and each is a text field of length 16. The field 'DiagnosisDesc' is a text field of length 255 with a text description of the diagnosis record.

Table 'ClinGuidelines' 340 contains information about the recommended clinical therapeutic guideline for a diagnoses. The other standard compliance information is contained in the table 'Compliance' 345. Clinical guidelines can consist of several steps that must be followed in order and or with a specific temporal relationship. To accommodate this the primary key for this table is a composite index of the fields 'ClinGuidelineID' and 'SeqNo. The field 'ClinGuidelineID' is a unique long integer generated by Microsoft Access using the counter attribute. The field 'SeqNo' is a number field with the value '1' for the first clinical guideline step. Subsequent guideline steps have an incremental value for the field 'SeqNo'. Each step of a clinical guideline can have a temporal value associated with it which is stored in the fields 'TimeWhen' which is a long integer field, and 'TimeUnits' which is a text field of length 8. For instance if a medication is to be taken 3 times per day then the value of 'TimeWhen' would be coded as the '3' and the value of 'TimeUnits' would be coded as 'times per day'. The field 'GuidelineText' is a text field of length 255 with the text of the step of the clinical guideline. The fields 'DiagnosisMaj' and 'DiagnosisMin' of table 'ClinGuidelines' 340 have a many-to-one primary-foreign key relationship with the fields 'DiagnosisMaj' and 'DiagnosisMin' of table 'Diagnoses' 335 and have the same attributes.

Table 'ClinGuidelines' has a Boolean field 'Recommended'. This is set to 'true' if the clinical guideline is the recommended treatment guideline. This is the guideline that the system will use when prompting medical personnel to enter treatment instructions. If the medical practitioner changes the recommended guideline by editing, adding or deleting or fully changing the recommended steps, and the new treatment instructions are inserted into the 'ClinGuidelines' table 340, with unique value for 'ClinGuidelineID', and 'SeqNo', and a value of 'false' for the field 'Recommended. In this manner, the table 'ClinGuidelines' 340 can have entries for a single 'Recommended' treatment guideline for a diagnosis, and can also contain multiple customized treatment guidelines for that same diagnosis.

Table 'Compliance' 345 contains standard compliance information about every diagnosis for the compliance categories 'alerts', 'followup', 'diagnosis information' and 'treatment information'. These are fixed by the system and in the preferred embodiment may not be edited by the health care practitioner. The primary key 'ComplianceID' is a unique long integer generated by Microsoft Access using the counter attribute. The field 'ComplianceType' is a text field of length 8 and identifies the type of compliance information contained in the record. It may take the values 'alerts', 'followup', 'daiginfo', or 'trtmnt' for 'alerts', 'followup', 'diagnosis information' and 'treatment information' respectively. The field 'ComplianceText' is a text field of length 255 and contains compliance specific descriptive information for the record. The field 'ComplianceURL' is a text field of length 255 and contains the URL of compliance specific descriptive information for the record. The fields 'DiagnosisMaj' and 'DiagnosisMin' of table 'Compliance' 345 have the same definition and attributes as the fields 'DiagnosisMaj' and 'DiagnosisMin' of table 'Diagnoses' 335.

The disease specific treatment and diagnosis information that will be made available to the patient is a URL or Internet resource. The system allows this information to be presented to the user according to the language preference of the patient. Table 'Patients' 305 contains a field 'PrefMedLang' which records the patients preferred language. When the patient uses the system to hyperlink to the disease or treatment information, the link is to an address that is modified by the language preference so the information is presented to the patient according to their preference. As an example, if the patient language preference has a value of 'Spanish' then when the patient hyperlinks to 'Diabetes/Mellitus' treatment information at the URL given in the Compliance table, the system will hyperlink to URL/Spanish so as to get the Spanish language version of the associated treatment information.

Table 'PatCompliance' 350 contains information about the treatment instructions that have been issued to a patient and the status of their compliance. The primary key 'PatComplIdx' is a unique long integer generated by Microsoft Access using the counter attribute. The field 'DiagnosisID' of table 'PatCompliance' 350 has a many-to-one primary-foreign key relationship with the field 'DiagnosisID' of table 'Diagnosis' 330 and has the same attributes. The field 'EncounterID' of table 'PatCompliance' 350 has a many-to-one primary-foreign key relationship with the field 'EncounterID' of table 'MedEncounter' 320 and has the same attributes. The field 'PatComplType' is a text field of length 8 and has a value representing the type of compliance information. It may take the values 'alerts', 'followup', 'diaginfo', 'trtmnt', or 'inst'. If it has one of the values 'alerts', 'followup', 'diaginfo', or 'trtmnt' then the field 'PatComplianceID' of table 'PatCompliance' 350 has a many-to-one primary-foreign key relationship with the field 'ComplianceID' of table 'Compliance' 345. If the field 'PatComplType' has the value 'inst' then the field 'PatComplianceID' of table 'PatCompliance' 350 has a many-to-one primary-foreign key relationship with the field 'ClinGuidelineID' of table 'ClinGuidelines' 340. The field 'dateAccessed' is a date field that contains a date and time stamp for when the patient accessed the treatment instructions and will be used by the system to calculate the patients measure of compliance. The field 'TrackIt' is a Boolean field. The default value is 'false' but can be set by the Medical Personnel to the value 'true'. If the value is 'false' then the system will not automatically generate reminder messages to the patient about the associated compliance item, if the patient is non-compliant. If the value is set to 'true' then the system will automatically generate reminder message if the patient is non-compliant FIG. 4 displays the definition of the patient's measure of compliance. In the preferred embodiment, every patient can be assigned a 'Measure of Compliance' 400 for any specific medical visit, or for any combination of 2 or more medical visits. For the one or more visits that are to be measured we count the 'Total items' that the patient is to access and the 'Visited items' that the patient has accessed. In the preferred embodiment compliance is only measured for medical visits more than one week old. These numbers can be calculated directly from the 'PatEncounter' table 360 of FIG. 3. First get the set of entries for the field 'EncounterID' 361 for the set of patient medical visits more than one week old that are to be measured. Since each medical visit is uniquely identified by the field EncounterID 361, the 'Total items' is defined as the number of records in the PatCompliance table 360 with an EncounterID in this set and a 'DateEncounter' more than one week old. The 'Visited items' is defined as the number of records in the PatCompliance table 360 with an EncounterID in this set and a non-null entry for the dateAccessed field 362 of the table PatCompliance 360. These two numbers are then compared. If the 'Total items' is equal to the 'Visited items' then the 'Measure of compliance' 400 for the patient's visits is 'Fully Compliant'. If the 'Visited items' is zero and the 'Total items is greater than zero then the 'Measure of Compliance' 400 for the patient's visits is 'Non-compliant'. If the 'Visited items' is less than the 'Total items' then the 'Measure of Compliance' 400 for the patient's visits is 'Partially compliant'. Other embodiments may use other means to measure a patient's compliance with medical care instructions.

C. User Interface

In this section we will describe the user interface for the system, and will display the main screens that the patient and medical personnel users of the system encounter. We will also explain the manner in which the user interface operates and the meaning and purpose of the button, labels, text boxes, check boxes, and drop-down boxes. A more detailed programmatic design for building the system is presented in following sections.

Figure 5:
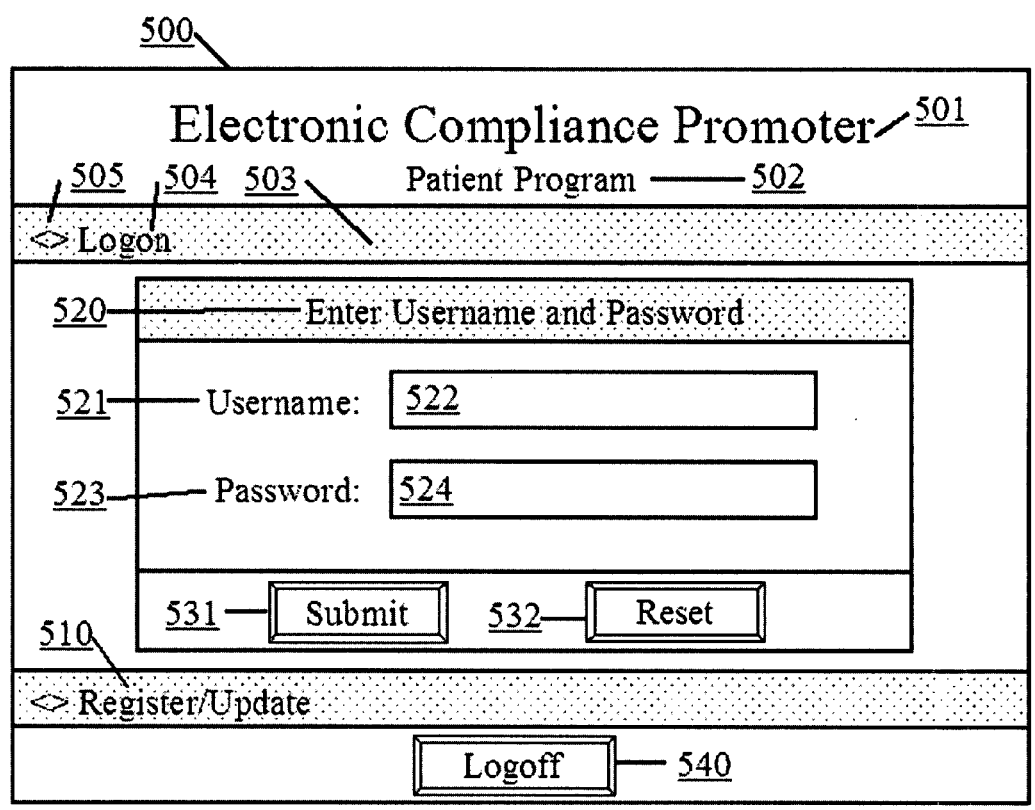
FIG. 5 is an example of the user-interface logon screen of the patient program.

FIG. 5 is an example 500 of the first screen presented to the patient on the display screen 201 that the patient encounters when they start the patient program. The purpose of the patient program is to allow the patient to review online their treatment instructions. A secondary purpose is to make a record of the information that is accessed by the patient-so the automatic compliance reminder feature of the system can be invoked.

This is the logon screen and the patient is not allowed to view their treatment instructions until they logon with an authorized Username and Password. It shows the title banner 501 for the system, 'Electronic Compliance Promoter' which will be displayed on all screens, and the specific program module, 'Patient Program' 502. Other program modules are the Medical Personnel data entry and administration modules.

A solid shaded bar 503 across the screen delineates sections of the module. Each section is labeled, and in this instance is labeled 'Logon' 504. There is another section header on the logon screen 500 labeled 'Register/Update' 510, which the patient uses to register an authorized Username/Password so they may access the system or to update their registration information. On the solid shaded bar is the symbol '< >' 505. System-wide, this is an indicator for expanding/contracting sections. In this case it means that by pointing and clicking the mouse anyplace on the solid shaded bar 503, the section will toggle to either expand or contract. In this figure the 'Logon' section 503 is shown expanded; i.e. all the fields of the section are displayed, and the 'Register/Update' section 510 is shown contracted with none of the fields of the section displayed.

Throughout the modules of the system similar functionality is employed and will reoccur in FIGS. 6 through 15. Whenever the symbol '< >' appears on a shaded bar it indicates that the information displayed in the section appearing immediately below it can be toggled to either fully display the data fields, or for the information displayed in the section to be hidden or contracted.

The information display items of the 'Logon' section 503 appear directly below the section bar. A display banner 'Enter Username and Password' 520 identifies the function of the screen which is to allow the user to type in the Username and Password and submit for authorization to review the patient's own treatment instructions. The label field 'Username' 521 identifies the data entry field 522 in which the patient enters their 'Username' and the label field 'Password' 523 identifies the data entry field 524 in which the patient enters their 'Password'. The Username and Password entries are validated against the 'Username' and 'Password' fields stored in the patient's record in the table 'Patients' 305 in the fields 'Username' and 'Password'.

The 'Logon' section has two buttons, 'Submit' 531 and 'Reset' 532. The 'Submit' button 531 causes the program to submit the entries in the data entry fields 522 and 524 to the treatment server program for patient authentication as the proper 'Username' and 'Password' respectively, waits for and displays the reply. The 'reset' button 532 causes the program to clear any key entries in the data entry fields 522 and 524 and set them back to their initial state.

In this example screen 500, the section 510 'Register/Update' is shown contracted so the data entry fields are not displayed. An example of this section in expanded view, caused by pointing and clicking anywhere in the shaded bar 510, will be shown in FIG. 6.

At the bottom of the 'Logon' screen is the button 'Logoff' 540. This button is selected by the user by pointing and clicking the mouse-pointing device at the button and causes the program to back to an initial state prior to any logon. If the patient has successfully logged in, and then selected the 'Logoff' button, they will not be allowed to review their treatment instructions until the again 'Logon' to the patient program. This 'Logoff' button 540 will be repeated on every screen of the Patient Module.

FIG. 6 is an example 600 of the first screen presented to the patient on the display screen 201 that the patient encounters when they start the patient program but with both 'Logon' section 504 and the 'Register/Update' section expanded to show all data entry fields. The patient would navigate from the display in FIG. 5 to the display in FIG. 6 by using the mouse pointer to point and click at the shaded bar 510 that is labeled 'Register/Update'. The program then redisplays the patient program screen as shown in FIG. 6. From FIG. 6 the user could return to the display as it appears in FIG. 5 by using the mouse pointer to point and click at the shaded bar 650 which will cause the program to collapse the 'Register/Update' section and hide the data entry fields. The 'Register/Update' data entry section has two purposes for the patient program. If it is invoked before the patient logs on then it is used to register the patient as a new user. This same section will be available to the patient after they have successfully logged onto the system. In that case, their current registration information is filled into the data entry fields of the 'Register/Update section and they can update their registration information by changing the information in a field and selecting the 'Submit' button 631 which causes the program to send the information to the treatment information server to be used to update the treatment information database, wait for and display the reply.

The data entry fields in the 'Register/Update' section include all of the fields in the Patient Table 305 except PatientID, DateEntered, DateUpdated, and MeasCompliance, which are managed by the database program. The data entry fields labeled Prefix 601, First Name 602, MI 603, Last Name 604, Suffix 605, Address 606, City 607, State 608, Zip 609, Phone 610, SSN 611, Email 612, Date of Birth 613, Sex 614 Marital Status 615, Language 616, Contact 617, Username 618, Password 619, and Med-Password 620, correspond respectively to the data fields, Prefix FName, MI, LName, Suffix, Address, City, State, Zip, Ph, SSN, Email, DOB, Sex, MaritalStatus, PrefMedLang, PrefMeansContact Username, Password, and PIN of the table Patients 305. When the user selects the 'Submit' button 631, the information is sent to the treatment information server for posting into the treatment information database, waits for and displays the reply.

Two of the fields, Language 616 and Contact 617 allow the patient to enter their preferences as a means of customizing how the system interacts with them. The choice of language 617 indicates that language by which the patient prefers to view treatment instructions, and the preferred means of contact 617 indicates the means by which the user prefers to receive reminder compliance notification.

Every patient has 2 Passwords. The Password field 'Password' 619 is used by the patient to access their treatment instructions from the patient program. In order for medical personnel to access a patients records and enter treatment instructions from the medical personnel data entry program, they have to have authorization from the patient in the form of the patients 'Username' 618 and 'Med-Password' 620 also called a 'PIN'. The 'Username' and 'Med-Password' field 620 or PIN allows access to the patient's information in the treatment instructions database from the medical personnel program but not the patient program. The 'Username' and 'Password' field 619 allows access to the patient's information in the treatment instructions database from the patient program but not from the medical personnel data entry program. The use of two Passwords provides a means by which the level of access and update control to patient's information can be provided for patients and medical personnel. The user may use the 'Register/Update' section 650 at any time to change the 'Username' 618, 'Password' 619, or 'Med-Password' 620.

Several of the fields have a down pointing arrow 605 on the right hand side of the data entry field. This indicates that the field is a drop-down box, and that the program already displays the only valid entries. The entries are accessed by using the mouse pointer to point and click at the arrow box 660 and a list of possible entries for the patient to select with the mouse pointer will be displayed. The allowable entries in the drop-down box field 'Prefix' 601 are 'Mr.', 'Mrs', 'Dr.', and 'Ms.'. The allowable entries in the drop-down box field 'Suffix' 605 are 'Ph.D.', 'DVM', 'Sr', and 'Jr'. The allowable entries in the drop-down box field 'State' 608 are all the 2-character standard abbreviations for the 50 states of the United States. The allowable entries in the drop-down box field 'Sex' 614 are 'M' and 'F' for male and female respectively. The allowable entries in the drop-down box field 'Marital Status' 615 are 'Married', 'Single', 'Divorced' and 'Widowed'. The allowable entries in the drop-down box field 'Language' 616 are 'English' and 'Spanish'. The allowable entries in the drop-down box field 'Contact' 617 are 'Email', 'Phone', 'Beeper', and 'Regular mail'.

The buttons 'Submit' 631, 'Reset' 632 and 'Logoff' 640 have the same functionality to that shown in the similarly named buttons 'Submit' 531, 'Reset' 532 and 'Logoff' 540 of FIG. 5.

Figure 7:
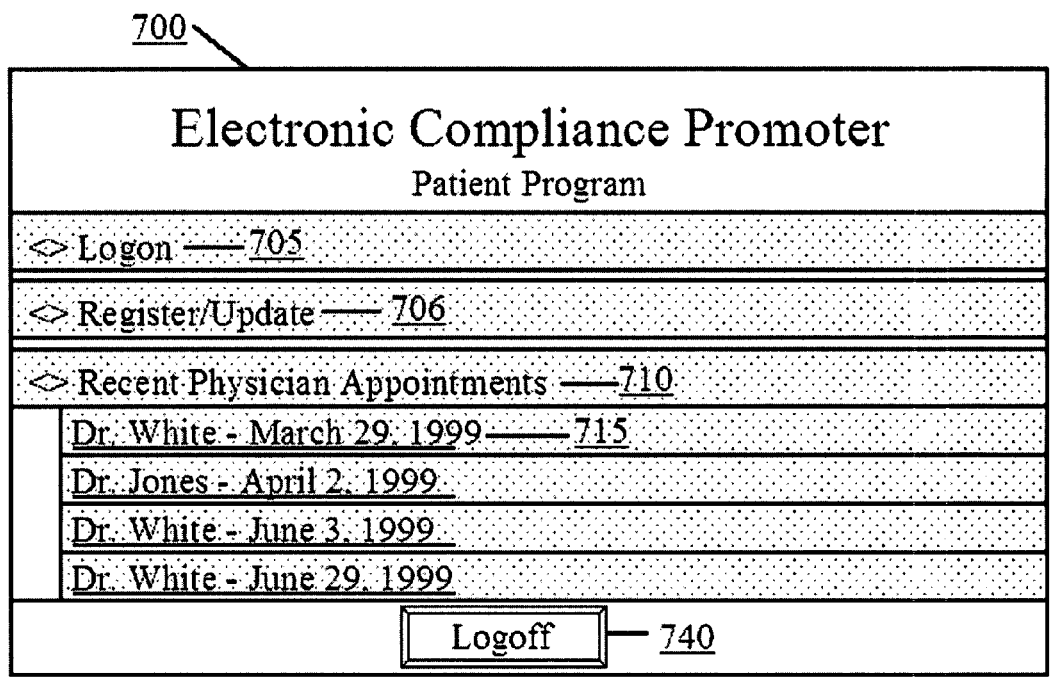
FIG. 7 is an example of the user-interface screen of the patient program showing the patient's office visits.

FIG. 7 is an example 700 of the list of the patient's medical appointments on the display screen 201 that are in the treatment information database and can be reviewed by the patient. In order to navigate to this screen, the user would have had to successfully log into the system with their Username and Password.

The display shows three shaded section bars, 'Logon' 705, 'Register/Update' 706, and 'Recent Physician Appointments' 710. Using the mouse pointer to point and click at any of these shaded bars will cause the program to collapse the display of the section if it is expanded, or to expand the display of the section if it is collapsed. In this example, the 'Logon' and 'Register/Update' sections are collapsed hiding their respective data entry fields and the 'Recent Physician Appointments' section 710 is in expanded mode.

The 'Recent Physicians Appointments' section 710 shows four recent appointments for the patient. The first appointment 715 shows an appointment with Dr. White on Mar. 29, 1999. Note that the appointment is underlined. The user can view the compliance information for that appointment by using the mouse pointer to point and click at the underlined appointment listing. This will cause the program to send a message to the treatment information server to retrieve the compliance information and redisplay the screen as in FIG. 8, with the specific compliance information from that appointment.

The button 'Logoff' 740 has the same functionality to that shown in the similarly named 'Logoff' 540 of FIG. 5.

FIG. 8 is an example 800 of the Patient Program screen on the display screen 201 that the patient encounters when they have selected a recent medical appointment to view. The display shows eight shaded section bars, 'Logon' 805, 'Register/Update' 806, and 'Recent Physician Appointments' 810, 'Treatment Instructions' 815, 'Alert' 820, 'Followup' 825, 'Diagnosis Information' 830, and 'Treatment Information' 835. Using the mouse pointer to point and click at any of these shaded bars will cause the program to collapse the display of the section if it is expanded, or to expand the display of the section if it is collapsed. In this example, the 'Logon', 'Register/Update', and 'Treatment Information' sections are collapsed hiding their respective data fields and the 'Recent Physician Appointments', 'Treatment Instructions', 'Alerts', 'FollowUp' and 'Diagnosis Information' sections are in expanded mode.

The section 'Recent Physician Appointments' 810 shows the data fields for the recent appointment 811 with Dr. White on Mar. 29, 1999. This section 812 shows appointment data fields that include the date, physician name, patient's complaint and the diagnosis. There is a scroll bar 813 that the patient may use to scroll through other appointments headers. The patient may select another appointment to view by using the mouse pointer to point and click at a session identifier 814 which will cause the patient program to send a request to the server to retrieve the information session information, wait for and display the reply.

The treatment instructions are displayed in the section 'Treatment Instructions' 815. The treatment information 816 for the selected appointment is displayed in a grid ordered according to the sequence and time order in which the instructions are to be followed. The alerts are displayed in the section 'Alerts' 820, and are a list of one or more alerts that the patient should be especially aware of. Alerts may be symptoms that should they occur the patient should seek immediate medical attention. The followup information is displayed in the section 'FollowUp' 825 and is a list of the medical followup, if any, that the user should schedule to continue medical treatment associated with their complaint. The diagnosis information is displayed in the section 'Diagnosis Information' 830, and in this case is a list of links to web sites that have relevant diagnosis information. The patient can use the mouse pointer to point and click at the links and retrieve the information pages for review. The treatment information is displayed in the section treatment Information 835. Similarly to the Diagnosis information, this section has links to web sites that have relevant treatment information. The diagnosis and treatment information will be presented to the user according to their language preference.

In the example of FIG. 8, the patient has accessed the instructions and information about their appointment on Mar. 29, 1999. For patient compliance purposes, the system records that the patient has accessed the treatment information for the March 29 appointment. The system will not record that the patient has accessed the treatment information for the other appointments until the patient specifically selects that appointment from the 'Recent Physician Appointment' sections 810 and brings the information up on the screen of the patient program.

The button 'Logoff' 840 has the same functionality to that shown in the similarly named 'Logoff' 540 of FIG. 5.

Figure 9:
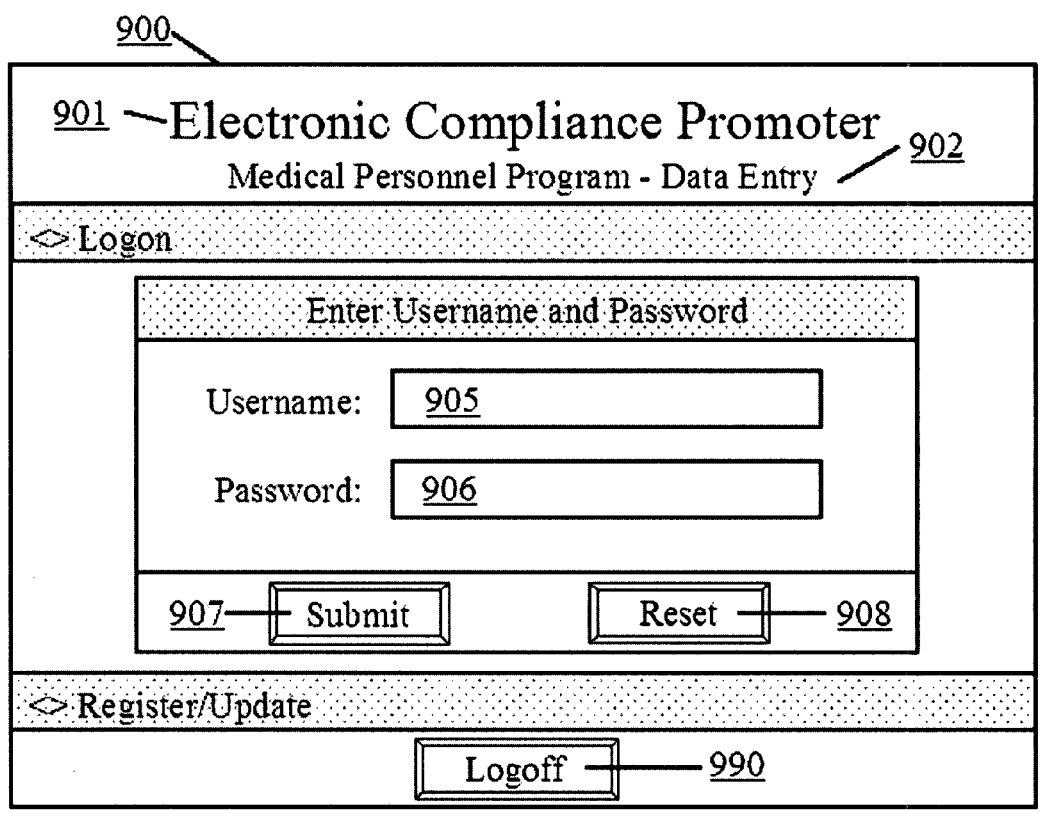
FIG. 9 is an example of the user-interface logon screen of the medical personnel data entry program

FIG. 9 is an example 900 of the first screen presented to medical personnel on the display screen 201 that medical personnel encounter when they start the medical personnel data entry program. The purpose of the medical personnel data entry program is for authorized medical personnel to enter the treatment instructions that are issued after a medical examination.

This is the logon screen and medical personnel are not allowed to invoke the patient data entry functions until they logon with an authorized Username and Password. The screen layout is entirely similar in layout and functionality to that of the patient program logon screen 500. For instance it shows the title banner 901 for the system, 'Electronic Compliance Promoter' which is the same as the title banner 501 for the patient program. The only difference in appearance is the name of the specific program module, 'Medical Personnel Program—Data Entry' 902.

Figure 11:
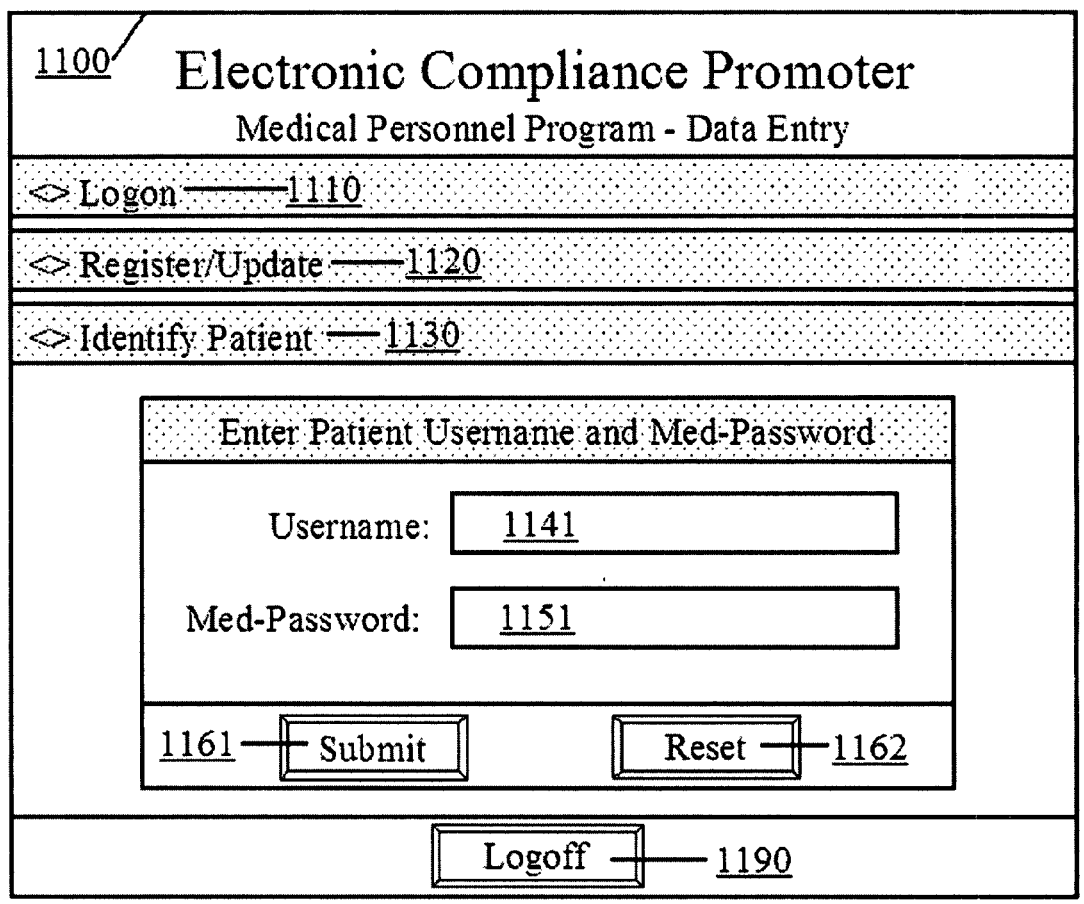
FIG. 11 is an example of the user-interface of the medical personnel data entry program used to enter the identity of the patient.

Functionally this data entry screen is similar to that of the patient program logon screen 500. The solid shaded bars work as in all screens—when selected by pointing and clicking the mouse anyplace on the solid bar, the section will toggle to either expand and display the data fields or contract to hide the data fields. The data entry fields 'Username' 905 and 'Password' 906 are the fields that the medical personnel use to enter their logon information to the system. After entering this information, selecting the 'Submit' button 907 sends the Username and Password to be validated against valid entries in the MedPersonnel table 310, and the program waits and displays the response. If the logon is validated the program redisplays the screen as shown in FIG. 11, and if it is not validated then this same logon screen is redisplayed. The 'Reset' button 908 causes the program to clear any entries from the fields labeled 'Username' 905 and 'Password' 906. The Logoff button 990 causes the program to terminate the Medical Personnel data entry session. If Medical Personnel had logged onto the system which provided them with access to patients records, then the Logoff function will deny them access until they again successfully logon.

FIG. 10 is an example 1000 of the first screen presented to the medical personnel on the display screen 201 that the patient encounters when they start the medical personnel data entry program. It shows the medical personnel data entry program of FIG. 9 but with the 'Logon' section 1005 contracted to hide the data fields and the 'Register/Update' section 1010 expanded to show the fields used for medical personnel to register to use the system or to update their logon information. The 'Register/Update' section has two purposes for the medical personnel program. If it is invoked before the medical personnel logs on then it is used to register the medical personnel as a new user. This same section will be available to medical personnel after they have successfully logged onto the system. In that case, their current registration information is filled into the data entry fields of the 'Register/Update' section and they can update their registration information by changing the information in a field and selecting the 'Submit' button 1031 which causes the program to send the information to the treatment instruction sever to be used to update the treatment instruction database, wait and display the reply.

The data entry fields in the 'Register/Update' section include all of the fields in the 'MedPersonnel' table 310 except MedPersID, DateEntered, and DateUpdated that are managed by the database program. The data entry fields labeled Prefix 1011, First Name 1012, MI 1013, Last Name 1014, Suffix 1015, Degree 1016, Medical Practitioner 1017, Address 1018, City 1019, State 1020, Zip 1021, Phone 1022, SSN 1023, Email 1024, Username 1025, and Password 1026, correspond respectively to the data fields, Prefix, Fname, MI, Lname, Suffix, Degree, MedPersType, Address, City, State, Zip, Ph, SSN, Email, Username, and Password of the table 'MedPersonnel' 310. When the user selects the 'Submit' button 1090, the information is sent to the treatment information server for posting into the treatment information database, and the program waits and displays the response. Several of the fields have a down pointing arrow on the right hand side of the data entry field. This indicates, as in the patient program, that the field is a drop-down box, and that the only valid entries are those displayed by the program. The buttons 'Submit' 1031, 'Reset' 1032 and 'Logoff' 1090 have similar functionality to that shown in the similarly named buttons 'Submit' 907, 'Reset' 908 and 'Logoff' 990 of FIG. 9.

FIG. 11 is an example 1100 of the first screen on the display screen 201 presented to the Medical personnel after they have successfully logged onto the system. The purpose of this screen is to allow the medical personnel to identify the patient for whom they will data enter medical examination compliance information. The display shows three shaded section bars, 'Logon' 1110, 'Register/Update' 1120, and 'Identify Patient' 1130. Using the mouse pointer to point and click at any of these shaded bars will cause the program to collapse the display of the section if it is expanded, or to expand the display of the section if it is collapsed. In this example, the 'Logon' and 'Register/Update' sections are collapsed hiding their respective data entry fields and the section 'Identify Patient' 1130 is in expanded mode. The medical personnel would enter the Username and Med-Password or PIN of the patient into the fields labeled 'Username' 1141 and 'Med-Password' 1151. The Med-Password is the Password that is setup by the patient to allow medical personnel to perform data entry and administration of their office visit compliance information, and is provided by the patient to the Medical personnel. The medical personnel would then select the 'Submit' button 1161 which would send the values in the fields labeled 'Username' 1141 and 'Med-Password' 1151 for authorization and wait and display the results. If the authorization is successful then the screen of FIG. 12 is displayed, but if it is not successful then this screen of FIG. 11 is redisplayed. If the medical personnel select the reset button then the entries in the fields labeled 'Username' 1141 and 'Med-Password' 1151 would be cleared of their entries. The Logoff button 1190 has the same functionality as the similarly named button 990.

FIG. 12 is an example 1200 of the screen on the display screen 201 used by the medical personnel to enter the compliance information for a patient's office visit. The purpose of this screen is for the medical personnel to enter the treatment instruction information for the patient's office visit. The display shows five major sections 'Logon' 1205, 'Register/Update' 1210, 'Identify Patient' 1215, 'Recent Physician Appointments' 1220, and 'Office Visit' 1230. The first three sections have the same functionality as in FIGS. 10 and 11. Note that by selecting the 'Identify Patient' 1215 section, the medical personnel will be presented with the 'Enter Username and Med-Password' logon screen of FIG. 11, and can enter the Username and Med-Password to work with a different patient. They can therefore work with a different patient without having to go through the Medical Personnel Login again. The section 'Recent Physician Appointments' 1220 lists prior appointments that have already been recorded in the system. In this example two prior appointments are shown and both are underlined, which indicates that by using the mouse pointer to point and click at the appointment, will bring up a screen that displays the specifics of that appointment.

The section 'Office Visit' 1230 is the section in which the treatment instructions are entered. First there is a section 1232 with the date of appointment to be entered, and the Physician, and the complaint. Below that there is a drop-down box field in which the diagnosis is entered. For each diagnosis selected the medical personnel specifies whether to include 'Treatment instructions' 1251, 'Diagnosis Information' 1252, 'Treatment Information' 1253, 'FollowUp' 1254, or 'Alerts' 1255. For each of these types of information the medical personnel can put an 'x' in the checkbox 'Include' 1256 to include the associated treatment instruction. If the checkbox is left blank then the associated information is not included in the treatment instructions. The medical personnel also use a checkbox 'Compliance Tracking' 1257 in a similar fashion to indicate to the system whether the treatment instructions included for the patient should be tracked automatically by the system and compliance reminders sent if the patient is non-compliant. This button can only be selected if the associated treatment instruction has been 'included' 1256.

The treatment instructions can be viewed in the 'Treatment instructions' section 1251. When the user points and clicks at this section the recommended treatment guidelines are displayed in a popup dialog window with the sequence of treatment guidelines displayed in a text grid. Medical personnel can edit these instructions. Any modification to the treatment guidelines results in the information being inserted into the ClinGuidelines table 340 with a unique ClinGuidelineID and SeqNo.

On this screen the Save button 1290 causes the Medical Personnel data entry program to send the office visit information, diagnosis, and treatment instruction information to the treatment instruction server and redisplay the screen as in FIG. 11.

Figure 13:
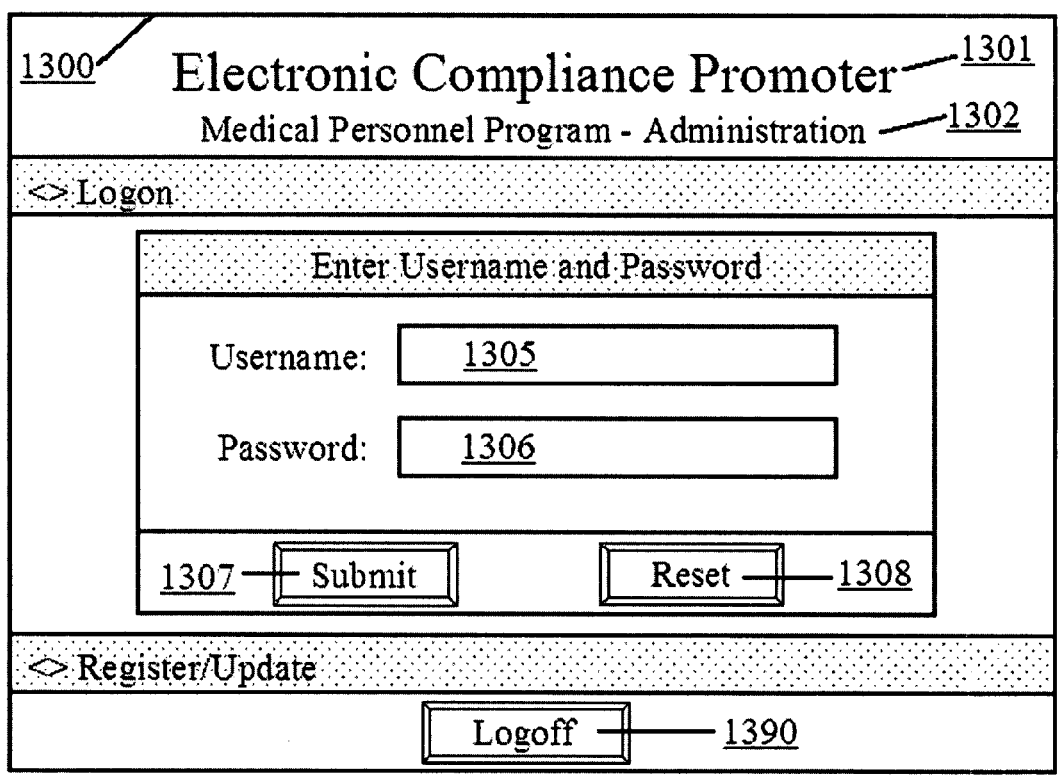
FIG. 13 is an example of the user-interface logon screen of the medical personnel administration program.

FIG. 13 is an example 1300 of the first screen presented to medical personnel on the display screen 201 that medical personnel encounter when they start the medical personnel administration program. The purpose of the medical personnel administration program is to allow authorized medical personnel to review the compliance of patients with their prescribed medical instructions.

This is the logon screen and medical personnel are not allowed to invoke the administration functions until they logon with an authorized Username and Password. The screen layout is entirely similar in layout and functionality to that of the patient program logon screen 500 and to that of the medical personnel data entry program 900. For instance we show the title banner 1301 for the system, 'Electronic Compliance Promoter' which is the same as the title banner 501 for the patient program and as the title banner 901 for the medical personnel data entry program. The only difference in appearance is the name of the specific program module, 'Medical Personnel Program-Administration' 1302.

Figure 14:
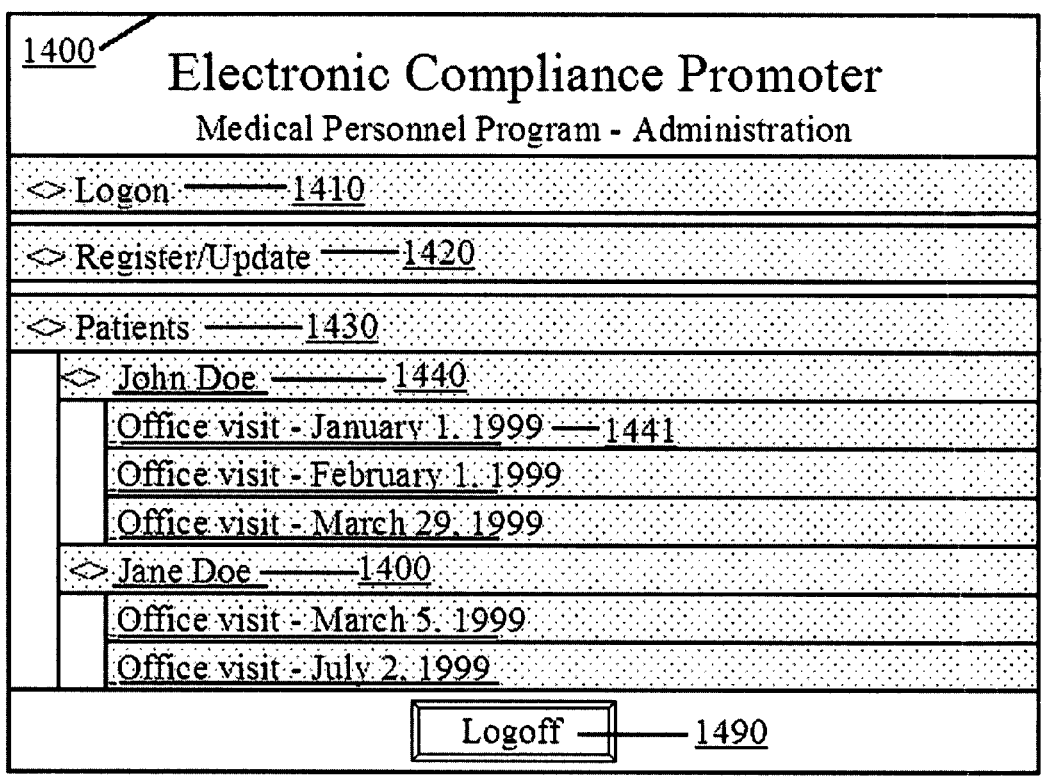
FIG. 14 is and example of the user-interface of the medical personnel administration program showing the list of all patients, by visit, who have been seen by the designated medical personnel.

Functionally this data entry screen is similar to that of the medical personnel data entry 900. The solid shaded bars work as in all screens—when selected by pointing and clicking the mouse anyplace on the solid bar the section will toggle to either expand and display the fields or contract to hide the fields. The data entry fields 'Username' 1305 and 'Password' 1306 are the fields that the medical personnel use to enter their logon information to the system. After entering this information, selecting the 'Submit' button 1307 sends the values in the fields labeled 'Username' 1305 and 'Password' 1306 to be validated against valid entries in the 'MedPersonnel' table 310, and the program waits and displays the results. If the logon is validated the program redisplays the screen as shown in FIG. 14. If the logon is not validated then the screen of FIG. 13 is redisplayed. If the medical personnel select the 'Reset' button 1308 by using the mouse pointing device to point and click at button, then the data entry fields 'Username' 1305 and 'Password' 1306 are cleared of any entries. The 'Logoff' button 13990 causes the program to terminate the Medical Personnel administration session. If Medical Personnel had logged onto the system which provided them with access to patients records, then the 'Logoff' function will deny them access until they again successfully logon.

FIG. 14 is an example 1400 of the screen presented to the medical personnel on the display screen 201 when they have first successfully logged into the system. The display shows five shaded section bars. The sections 'Logon' 1410 and 'Register/Update' 1420 are the same as described in FIGS. 12 and 13. There is a new section 'Patients' 1430 which lists all patients that the Medical Personnel may review. This section has its own sections—one for every patient listed. In this example there are just two patients John Doe and Jane Doe. The office visits for John Doe are listed in the section 'John Doe' 1440 and the office visits for Jane Doe are listed in the section 'Jane Doe' 1450. The data fields for the patient specific sections are the list of office visits for that patient. Each entry 1441 in the list is underlined which indicates that by using the mouse device to point and click at the office visit entry, compliance information for that office visit will be displayed. The 'Logoff' button 1490 has the same functionality as the similarly named button 1390.

FIG. 15 is an example 1500 of the compliance status screen presented to the medical personnel on the display screen 201 when they have selected a patient for review. In this case the medical personnel has selected to review the compliance information for the patient Jane Doe. The display shows seven shaded section bars. The sections 'Logon' 1505 and 'Register/Update' 1510 are the same as described in FIGS. 13 and 14. There is a new section 'Patients'—Jane Doe' 1520 under which the compliance information for the patient Jane Doe will be displayed. Each office visit (1530, 1531) is presented as its own section in descending chronological order. Within each office visit, there is a section displaying the compliance information for each diagnosis 1540. If there are multiple diagnoses at an office visit then each diagnoses is displayed in its own section. The compliance information that is presented is for five categories of compliance information—'Treatment instructions' 1550, 'Diagnosis Information' 1555, 'Treatment Information' 1560, 'Alerts' 1565 and 'FollowUp' 1570. For each category the information about whether the patient has accessed the information is contained in a checkbox 'Accessed' 1541. If the checkbox has an 'x' in it then the patient has accessed the corresponding type of information. If the checkbox is empty then the patient has not accessed the corresponding type of information. The medical personnel uses the checkbox 'Send reminder' 1542 to explicitly request the system to send a reminder compliance message to the patient. If the medical personnel places and 'x' in the checkbox, by using the mouse pointing device to point and click at the checkbox, then a reminder compliance message will be sent by the treatment server program to the patient. The 'Back' button 1580 will cause the program to redisplay the prior screen with a list of the visits for all patients as shown in FIG. 14. The 'Logoff' button 1590 has the same functionality as the similarly named button 1390.

D. Compliance Reminders

Compliance reminders are one of the key features of the invention. The "Measure of Compliance" 400 provides a reasonable surrogate measure for actual compliance, and is used by the system to track a patients access to the treatment information resources. All patients that are not fully up-to-date in reviewing the treatment information are automatically sent reminders.

FIG. 16 is an example 1600 of an Email reminder that is sent automatically by the treatment information database program to a patient who is not fully compliant with the post-examination treatment instructions as measured by the 'Measure of Compliance' 400. It is a standard Email message addressed to the patient in the 'To' Email address 1610, sent by the Electronic Compliance Promoter identified in the 'From' Email address 1620, and with a subject line 1630 indicating to the patient that this is a reminder about the Mar. 29, 1999 office visit. The body of the E-mail further references the patient's medical examination by listing the complaint 1640 at the time of the office visit and the diagnosis 1650. A short message 1660 reminds the patient to check information relevant to the referenced office visit.

E. Communication Protocol

The preferred embodiment uses an industry standard Ethernet and an industry standard TCP/IP network protocol for its computer network. A computer network conversation between the patient program and the treatment database program is implemented by establishing a connection between the computers over the computer network. Similarly, a computer network conversation between the medical personnel program and the treatment database program is implemented by establishing a connection between the computers over the computer network. Similarly, a computer network conversation between the medical personnel administration program and the treatment database program is implemented by establishing a connection between the computers over the computer network.

To minimize the computer resources utilized to maintain these connections, this invention uses a non-persistent network connection; i.e. a network connection is established between the client and server computers only for the length of time necessary to perform a specific transaction.

In the preferred embodiment the connections are implemented using the industry standard hypertext transport protocol (http). In other embodiments the non-persistent connection may be implemented using another industry standard protocol, or a special non-persistent protocol may be implemented specifically to address the operation of this system. If any of the client programs (patient program, medical personnel program or medical personnel administration program) or the treatment database program terminates their connection with the other program, either by design or another reason, such as a network outage, the other program also terminates its connection state.

F. Patient Program

In this preferred embodiment of the program the client programs all execute as industry standard hypertext markup language (html) pages in a Microsoft Internet Explorer Web Browser Version 4.0. The treatment instructions database server program executes as Microsoft Active Server Pages running under the Microsoft Internet Information Server 4.0 web server. The writing of client side html code that implements functionality within a web browser is well-known to those skilled in the arts, as is the writing of Active Server Page to generate the content of these pages dynamically based on input from the user and information contained within a database. Thus both the client and server programs utilize the services of standard well-known and well-used web systems programs to implement their functionality. The operation of these system programs are well known to those skilled in the art and will not be further described in this specification.

In the preferred embodiment the specific language protocol versions that are used are the Hypertext Markup Language 4.0 standard and the Cascading Style Sheet (CSS) 1.0 standard. The Microsoft Internet Explorer is using Active Server Pages 2.0 to generate html pages dynamically, and the ActiveX Data Objects Component (ADO) to access data in the treatment instructions database. An example of how these standards are utilized may be helpful.

The operation of the preferred embodiment of the client programs all rely heavily on sections of information that are toggled to expand and contract when the user points and click with the mouse pointer device at the section header. For instance FIG. 5 show a 'Register/Update' section 510 in collapsed mode. In FIG. 6 this same 'Register/Update' section 650 is shown in expanded mode. Throughout the specification of the client programs, expanding and collapsing of sections is implemented using specific features of the HTML 4.0/CSS 1.0 standards. Expanding a section displays the information for the user and collapsing has the opposite effect. Since the client programs are running under a web browser, and are written in HTML 4.0 and CSS 1.0, the expand/collapse functionality is implemented using the HTML DIV start and end tags to define screen sections, and then setting the properties of the style attribute to cause the browser to either display or hide the section. Thus the expand/collapse function is standard functionality that can be employed in any web page that is written in HTML 4.0/CSS 1.0 and operates within the confines of the Microsoft Internet Explorer Web Browser Version 4.0. This is standard html programming that is well known to any person skilled in the art.

Similarly, after the client program is first displayed there will be one or more 'Submit' buttons displayed. Selecting a 'Submit' button by pointing and clicking with the mouse pointer device will cause the Web browser to access and display on the display screen a new page associated with a URL. This is implemented in all client programs by use of the html FORMS tags with the value of the action attribute set to the URL of the client program and name-value pairs of the QueryString set by the web browser when the user select a 'Submit' button. This too is standard html programming understood and well known to those skilled in the art. The 'Reset' button is also used throughout the client programs, always in tandem with the 'Submit' button. The 'Reset' button resets all fields contained within the FORMS tag to their initial values, and is standard html programming understood and well known to those skilled in the art.

Finally, throughout the client programs we use hyperlinks. This is indicated by underlined test. By pointing and clicking with the mouse pointer device at a hyperlink, will cause the web browser to display the URL referenced by the hyperlink. Hyperlinking is central to the notion of web programming, is standard html programming understood and well known to those skilled in the art. In some instances the hyperlink information will be displayed in a new window that 'floats' on top of the client program. This too is a general facility of web programming that is well known to those skilled in the art.

Similarly with other functionality of the client programs, the means by which the functionality is implemented are standard html/css coding and are well known to those skilled in the art. The specification will therefore focus on the logic of the systems and the algorithms employed to implement the systems. For each of the three client programs, Patient, Medical Personnel data entry, and Medical Personnel administration programs, we provide the description by means of the standard systems design tools—state diagrams and state tables.

Figure 17:
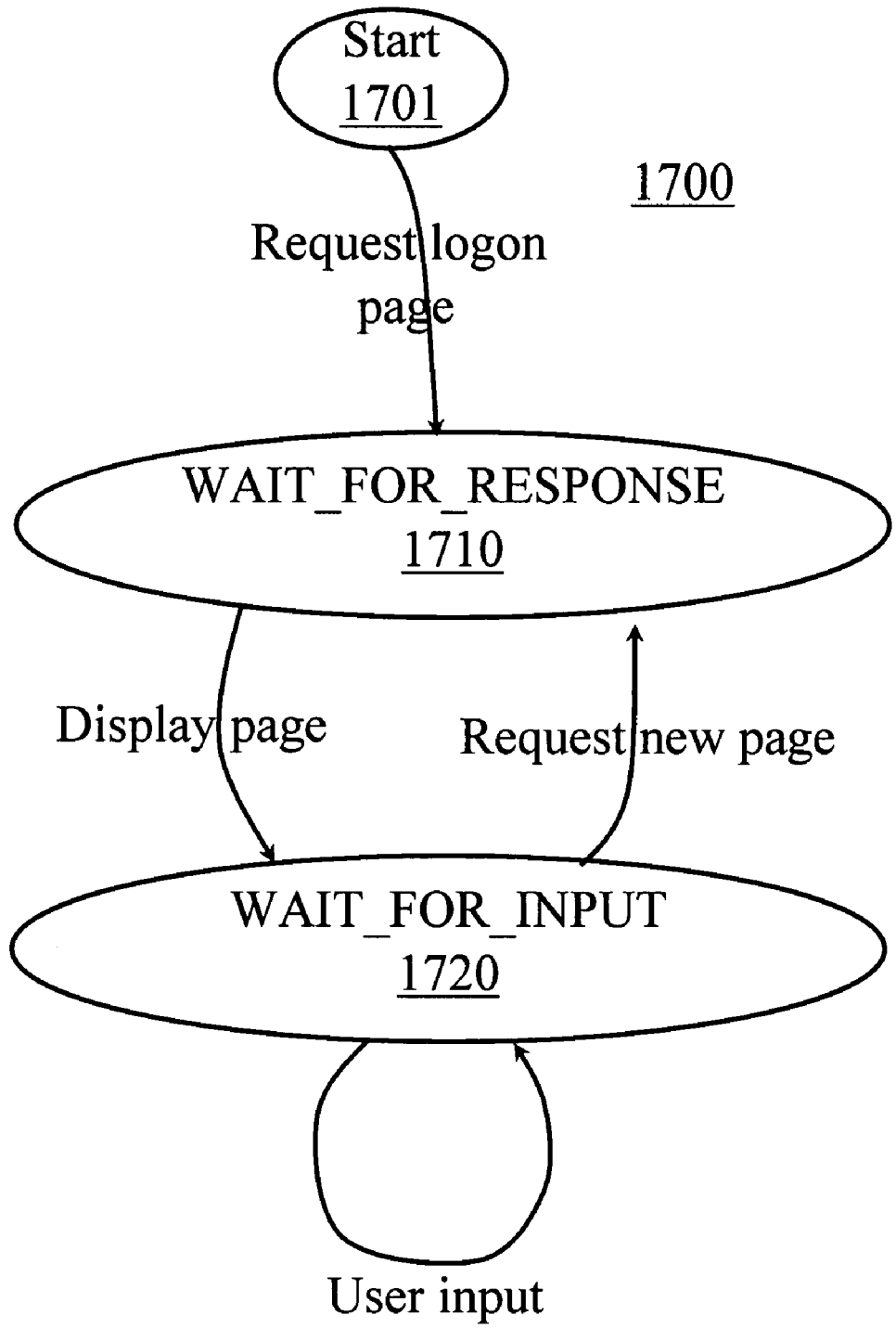
FIG. 17 is a state diagram describing the operation of the patient program.

FIG. 17 is a state diagram 1700 showing the state machine describing the logical operation of the patient program. The state diagram shows the different states that the program may occur in, and the actions that cause them to change to another state.

Since the patient program is operating under the Microsoft Internet Explorer Web Browser 4.0, after starting the Patient Program the patient program is either waiting for a response from the server program or waiting for input from the user. State 'START' 1701 represents the program state when the Web Browser is started and a request is sent via http to the server program for the patient logon page. After sending the request the program immediately transfers to the 'WAIT_FOR_REPONSE' 1710 state, awaiting the receipt via http of the html file that will display the requested logon page of the Patient program on the display screen of the Web Browser. When the html file is received it is displayed or rendered by the browser on the display screen and then processing transfers to the 'WAIT_FOR_INPUT' 1720 state in which the Patient Program awaits user keyboard or computer mouse input.

There are two distinct type of actions that may occur in the 'WAIT_FOR_INPUT' 1720 state. The user may interact with the screen as when they use the mouse to point-and-click at a section to expand or contract it, or key enter information in one of the data entry fields displayed on the screen. This type of interaction between the user and the program results in changes to the currently displayed screen but does not cause a request to be sent to the server program for a new page. In this case the program processes the user input and remains in the state 'WAIT_FOR_INPUT' 1720.

The second type of action that may occur is when the user initiates an action, such as pressing the 'Submit' button 540 of FIG. 5, which causes a http request message to be sent to the server requesting a new page. In this case the message is sent and the program transfers to the state 'WAIT_FOR_REPSONSE', awaiting the reception of a new page. When that page is received, it is displayed on the display screen of the Web Browser and the program transfers to the state 'WAIT_FOR_INPUT' awaiting action from the user.

The state machine for the Patient Program 1700 clearly shows the reliance on the browser and the server programs for the operation of this module of the system. The browser is the operational platform that displays html pages and interacts with the user. The user may initiate actions that will result in a message to the server to formulate a new html page, wait for the response from the server, and display a new page of the patient system according to the specifics of the message request.

FIG. 18 is a state table 1800 for the operation of Patient Program. It has 3 states, START 1801 which corresponds to the state 1701 of FIG. 17, WAIT_FOR_RESPONSE 1810 which corresponds to the state 1710 of FIG. 17, and WAIT_FOR_INPUT 1820 which corresponds to the state 1720 of FIG. 17. The state table provides more detail on the operation of the Patient Program.

When the Patient Program is started it immediately enters the logical state START 1801 in which the Internet Explorer Web browser program is started in the 'StartUp' operation 1802. The Web Browser uses the Universal Resource Locator (URL) of the Patient Program to request the html file with the logon screen for the Patient Program. In this case the URL is only the name of the Network Resource with the Patient Program ASP file and has no 'QueryString' associated with it. After requesting the file, the program transfers to the state WAIT_FOR_RESPONSE 1810 and when the file is received, performs the operation 'Display web page' 1811 and displays the Patient program logon screen, sets the focus to the 'Logoff' button 540 of FIG. 5, and transfers to the state 'WAIT FOR INPUT' 1820.

The state 'WAIT_FOR_INPUT' 1820 is the state in which the user interacts with the Patient Program and so it is in this state that most of the html/css programming is done. There are 10 different operations that the program must be capable of handling.

If the operation is to 'Expand or Collapse' a section 1821 then if the selected section is in collapsed mode then the screen is redisplayed with the selected section in expanded mode. If the selected section is in expanded mode then the screen is redisplayed in collapsed mode. In the preferred embodiment the sections are set to their respective modes by programming the DHTML 'onclick' event to set the style property display attribute of the sections html DIV tag to 'NONE' to collapse the section and 'BLOCK' to display it.

If the operation is to 'Change focus' 1827 then the browser resets the focus to the selected field. This will most often occur with the data entry fields. For instance if the user is entering a Username into the Username field 522 of FIG. 5, then the focus of the browser has to be on this data entry field so the browser will update the Username data entry field with the keyed values. The web browser changes the focus when the user points and clicks at a data entry field or uses the 'Tab' key to navigate to a new field. If the operation is 'Key-Entry' 1828, then the key entered is appended to the values in the data entry field that has the focus. This operation is handled by the web browser and includes support for 'Backspace' and 'Del' to remove previously keyed characters.

If the operation is to 'Submit Logon' 1823 then the Web Browser submits a request to the server program to validate the Username and Password of the user. The Web Browser uses the Universal Resource Locator (URL) of the Patient Program with the 'QueryString' set to name-value pairs with the Username and Password. This URL request is sent to the server and the program enters the state 'WAIT_FOR_REPONSE' 1810 waiting to receive and display a new page of the Patient Program. If the treatment database server program can validate the Username and Password then it will respond with a screen containing Patient Information including recent appointments. If the treatment database server program cannot validate the Username and Password then it will respond with the Patient Program logon screen.

If the requested operation is to 'Submit SignUp/Update' 1824 then the Web Browser submits a request to the server program to either sign-up a new patient or to update the patient's information in the treatment instructions database. The Web Browser uses the URL of the Patient Program with the QueryString set to the name-value pairs of the 'Register/Update' section 650 of FIG. 6. This URL request is sent to the server and the program enters the state 'WAIT_FOR_RESPONSE' 1810 waiting to receive and display a new page of the Patient Program. If the SignUp is successful then the user will be able to further use the system. However at the time of registration there will be no medical appointments in the system so there will be no treatment instruction information to review. If the update is successful, then they will be logged into the system, if not already logged in, and the server will respond with the same screen as after a successful 'Submit Logon' 1823.

If the requested operation is 'Submit Recent Appointment' 1825, then the patient is requesting to review the treatment information for a selected appointment. The Web Browser uses the URL associated with the underlined (hyperlink) appointment 715 of FIG. 7 to request a new Patient Program screen with the appointment information. The URL request is sent to the server and the program enters the state 'WAIT_FOR_RESPONSE' 1810 waiting to receive and display a new page, similar to FIG. 8, with the patient's treatment instruction information for the specified medical appointment.

For both the patient 'Logon' section and the 'SignUp/Update' section there is a 'Reset' button. If the selected operation is 'Reset' 1822, then the data entry fields associated with the respective sections are cleared to their initial state with no entries.

If the requested operation is 'Display Diagnosis Info' 1829, then the patient has selected a hyperlink to a website that contains diagnosis information. The Web browser opens a new browser window and displays the hyperlink URL with the diagnosis information. This will cause the system to hyperlink to the resource in the language preference of the patient by linking to a subdirectory of the URL with the language specific information. For instance if the value of the Patients language preference is 'Spanish' then the system may access information about Diabetes/Mellitus at the network site URL/Spanish/DiabetesMellitus.html. The window will 'float' on top of the Patient program window and will remain displayed until the Patient closes it. The Patient Program remains fully operational even while the web browser manages the second diagnosis information window.

If the requested operation is 'Display Treatment Info' 1830, then the patient has selected a hyperlink to a website that contains treatment information. The Web browser opens a new browser window and displays the hyperlink URL with the treatment information. Analogously to disease information, treatment information is displayed in the language preference of the patient. The window will 'float' on top of the Patient program window and will remain displayed until the Patient closes it. The Patient remains full operational even while the web browser manages the second treatment information window.

If the requested operation is 'Submit Logoff' 1826, then the Web Browser submits a request to the server program to log the patient out of the system. The program uses the URL of the Patient Program with the QueryString indicating 'Logoff'. The URL request is sent to the server and the program enters the state 'WAIT_FOR_RESPONSE' 1810 waiting to receive and display a new 'Logon' pages just as if it had transitioned from the 'Start' state 1801.

G. Medical Personnel Program

Figure 19:
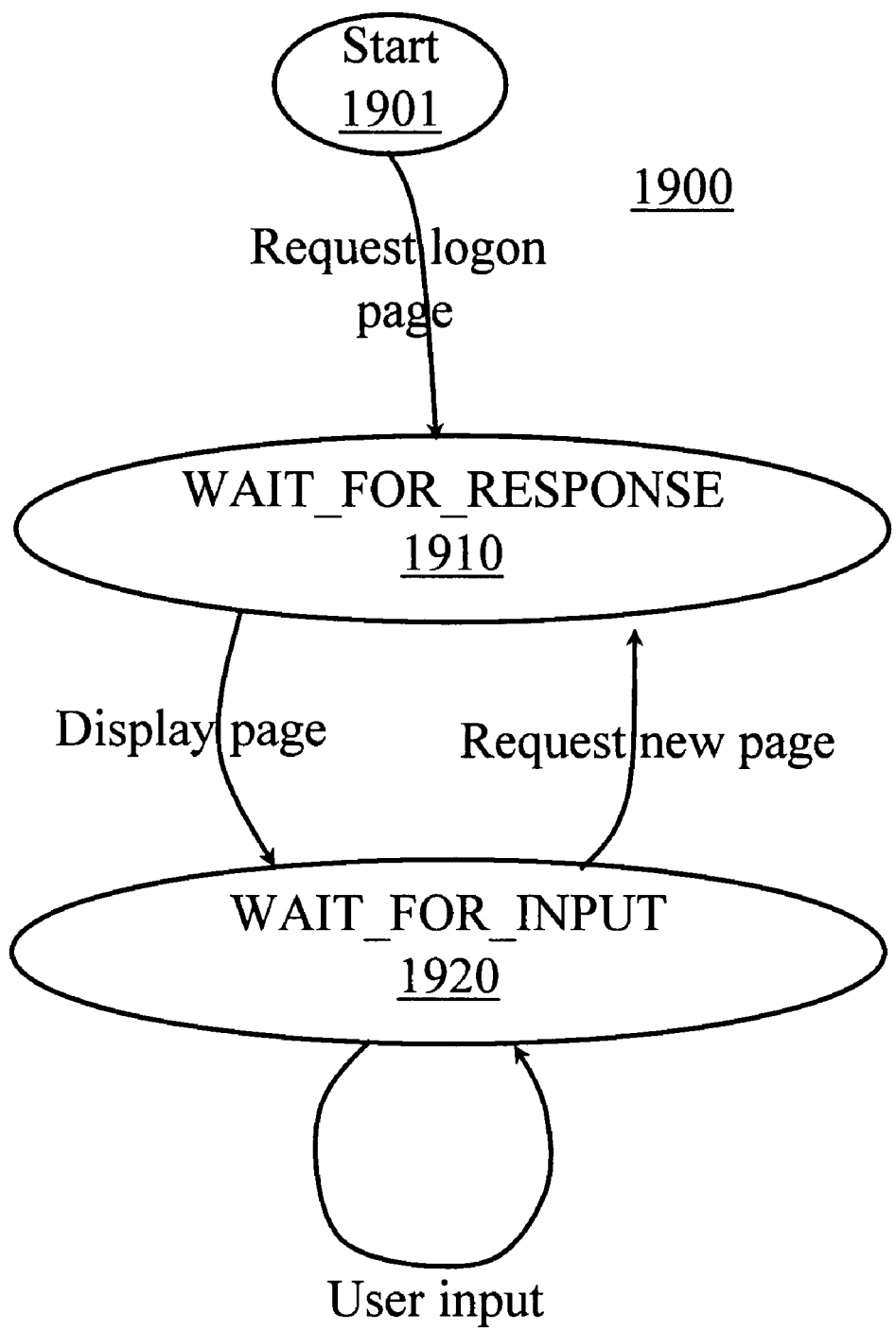
FIG. 19 is a state diagram describing the operation of the medical personnel data entry program.

FIG. 19 is a state diagram 1900 showing the state machine describing the logical operation of the Medical Personnel Data Entry Program. Since the Medical Personnel Data Entry Program is operating under the Microsoft Internet Explorer Web Browser 4.0, after invocation the program is either waiting for a response from the server program or waiting for input from the user. State 'START' 1901 represents the program state when the Web Browser is started and a request is sent via http to the server program for the Medical Personnel logon page. After sending the request the program immediately transfers to the 'WAIT_FOR_REPONSE' 1910 state, awaiting the receipt via http of the html file that will display the requested logon page of the Medical Personnel Data Entry Program on the display screen of the Web Browser. When the html file is received it is displayed or rendered by the browser on the display screen and then processing transfers to the 'WAIT_FOR_INPUT' 1920 state in which the Medical Personnel Data Entry Program awaits user keyboard or computer mouse input.

There are two distinct type of actions that may occur in the 'WAIT_FOR_INPUT' 1920 state. The user may interact with the screen as when they use the mouse to point-and-click at a section to expand or contract it, or key enter information in one of the data entry fields displayed on the screen. This type of interaction between the user and the program results in changes to the presently displayed screen but does not cause a request to be sent to the browser for a new page. In this case the program processes the user input and remains in the state 'WAIT_FOR_INPUT' 1920.

The second type of action that may occur is when the user initiates an action, such as pressing the 'Submit' button 907 of FIG. 9, which causes a http request message to be sent to the server requesting a new page. In this case the message is sent and the program transfers to the state 'WAIT_FOR_REPSONSE' 1910, awaiting the reception of a new page. When that page is received, it is displayed on the display screen of the Web Browser and the program transfers to the state 'WAIT_FOR INPUT' awaiting action from the user.

The state machine for the Medical Personnel Program 1900 clearly shows the reliance on the Web Browser and the Web Server for the operation of this module of the system. The browser is the operational platform that displays html pages and interacts with the user. The user may initiate actions that will result in a message to the server to formulate a new html page, wait for the response from the server, and display a new page of the Medical Personnel Data Entry system according to the specifics of the message request.

FIG. 20 is a state table 2000 for the operation of Medical Personnel Data Entry Program. It has 3 states, START 2001 which corresponds to the state 1901 of FIG. 19, WAIT_FOR_RESPONSE 2010 which corresponds to the state 1910 of FIG. 19, and WAIT_FOR_INPUT 2020 which corresponds to the state 1920 of FIG. 19. The state table provides more detail on the operation of the Medical Personnel Data Entry Program.

When the Medical Personnel Data Entry Program is started it immediately enters the logical state START 2001 in which the Internet Explorer Web Browser program is started in the StartUp operation 2002. The Web Browser uses the Universal Resource Locator (URL) of the Medical Personnel Data Entry Program to request the html file with the logon screen. In this case the URL is the network resource of the Medical Personnel Data Entry ASP file and has no QueryString associated with it. After requesting the file, the program transfers to the state WAIT_FOR_RESPONSE 2010 and when the file is received, performs the operation 'Display web page' 2011 and displays the Medical Personnel Data Entry program logon screen, sets the focus to the 'Logoff' button 990 of FIG. 9, and transfers to the state 'WAIT_FOR_INPUT' 2020.

The state 'WAIT_FOR_INPUT' 2020 is the state in which the user interacts with the Patient Program and so it is in this state that most of the html/css programming is done. There are 14 different operations that the program must be capable of handling.

If the operation is to 'Expand or Collapse' a section 2021 then if the selected section is in collapsed mode then the screen is redisplayed with the selected section in expanded mode. If the selected section is in expanded mode then the screen is redisplayed in collapsed mode. In the preferred embodiment the sections are set to their respective modes by programming the DHTML 'onclick' event to set the style property display attribute of the sections html DIV tag to 'NONE' to collapse the section and 'BLOCK' to display it.

If the operation is to 'Change focus' 2030 then the browser resets the focus to the selected field. This will most often occur with the data entry fields. For instance if the user is entering a Username into the Username field 905 of FIG. 9, then the focus of the browser has to be on this data entry field so the browser will update the Username field. The web browser changes the focus when the user points and clicks at a data entry field or uses the 'Tab' key to navigate to a new field. If the operation is 'Key-Entry' 20, then the key entered is appended to the values in the data entry field that has the focus. This operation is handled by the web browser and includes support for 'Backspace' and 'Del' to remove previously keyed characters.

If the operation is to 'Submit MedPersonnel Logon' 2023 then the Web Browser submits a request to the server program to validate the Username and Password of the Medical Personnel. The Web Browser uses the Universal Resource Locator (URL) of the Medical Personnel Data Entry Program with the QueryString set to name-value pairs with the Username and Password. This URL request is sent to the server and the program enters the state 'WAIT_FOR_REPONSE' 2010 waiting to receive and display a new page of the Medical Personnel Data Entry Program. If the treatment database server program can validate the Username and Password then it will respond with a screen requesting patient logon information. If the treatment database server program cannot validate the Username and Password then it will respond with the Medical Personnel Data Entry Program logon screen.

If the operation is to 'Submit Patient Logon' 2024 then the Web Browser submits a request to the server program to validate the Username and PIN of the Patient so the Medical Personnel may enter treatment instruction information associated with the current medical appointment. The Web Browser uses the Universal Resource Locator (URL) of the Medical Personnel Data Entry Program with the QueryString set to name-value pairs with the Username and PIN. This URL request is sent to the server and the program enters the state 'WAIT_FOR_REPONSE' 2010 waiting to receive and display a new page of the Medical Personnel Data Entry Program. If the treatment database server program can validate the Username and PIN then it will respond with a screen similar to FIG. 12 in which the medical personnel may enter the treatment instruction information associated with the medical appointment. If the treatment database server program cannot validate the Username and PIN then it will respond with a screen similar to FIG. 11, in which the medical personnel has been validated but still requesting patient validation.

If the requested operation is to 'Submit SignUp/Update' 2025 then the Web Browser submits a request to the server program to either sign-up a new medical personnel or to update the medical personnel's information in the treatment instructions database. The Web Browser use the URL of the Medical Personnel Data Entry Program with the QueryString set to the name-value pairs of the 'Register/Update' section 1010 of FIG. 10. This URL request is sent to the server and the program enters the state 'WAIT_FOR_RESPONSE' 2010 waiting to receive and display a new page of the Medical Personnel Data Entry Program. If the SignUp or update is successful then they will be logged into the system, if not already logged in, and the server will respond with the same screen as after a successful 'Submit MedPersonnel Logon' 2023.

For both the Medical Personnel 'Logon' section, the Medical Personnel Program 'Enter Patient Username and Pin' section, and the 'SignUp/Update' section there is a 'Reset' button. If the selected operation is 'Reset' 2022, then the data entry fields associated with the respective sections are cleared to their initial state with no entries.

If the requested operation is 'Display Recent Appointment' 2032, then the Medical Personnel has selected to display the treatment information for a specific patient's appointment in a new web browser window. The Web browser opens a new browser window and displays the patient appointment. The window will 'float' on top of the Medical Personnel Data Entry program window and will remain displayed until it is closed. The Medical Personnel Data Entry Program remains fully operational even while the web browser manages the new patient appointment information window.

If the requested operation is 'Enter Diagnosis' 2026, then the Medical Personnel will use the mouse pointer device to open the drop-down diagnosis field 1235 of FIG. 12, and select a diagnosis for the patient. Scrolling down to other diagnoses and treatment instructions data entry fields enters additional diagnoses. These diagnoses will be entered into the treatment instruction database for the patient's medical visit when the medical personnel select the 'Save' button 1290.

If the user requested operation is 'Enter Include Treatment Information' 2027, then the Medical Personnel has selected to toggle a checkbox 1256 of FIG. 12, indicating that the patient should be instructed to use the associated information. Only if the checkbox is checked will the instructions be entered into the database. The posting of the indicated information to the treatment instruction database for a patient's medical visit occurs when the medical personnel select the 'Save' button 1290.

If the requested operation is 'Enter Track Treatment Information' 2028, then the Medical Personnel has selected to toggle a checkbox 1257 of FIG. 12, indicating that the system should track and automatically notify the patient about compliance to the associated treatment instructions. This checkbox can only be selected if the corresponding 'Include' checkbox 1256 has been checked. The posting of the indicated information to the treatment instruction database for a patient's medical visit occurs when the medical personnel select the 'Save' button 1290.

If the requested operation is 'Submit Logoff' 2029, then the Web Browser submits a request to the server program to log the Medical Personnel out of the system. The program uses the URL of the Medical Personnel Data Entry Program with the QueryString indicating 'Logoff'. This has the effect of nullifying the Medical personnel logon to the system and displaying the screen as in FIG. 8.

If the requested operation is 'Save' 2033 then the medical personnel has entered the appointment specific information and is requesting that it be saved in the treatment instructions database. If treatment instruction information has been entered, then the values from the office visit section of FIG. 12 are included in the QuerySring name-value pairs that are sent to the server. The URL request is sent to the server and the program enters the state 'WAIT_FOR_RESPONSE' 2010 waiting to receive and display a patient login page as in FIG. 11.

If the requested operation is 'Enter Treatment Instructions' 2034 then the medical personnel has chosen to modify the recommend treatment guidelines for the associated diagnosis. The section '1251' will redisplay as a popup dialog box with the recommended treatment guidelines in an editable text grid. The medical personnel can edit, delete and change the treatment instructions and close the popup dialog box. Making any change has the effect of changing the value of the html TreatmentEdit field to 'true'. The default value is 'false'. This html field is hidden from the user but its value is sent to the server along with other name-value pairs when the 'Save' button 1290 is invoked. The server will use this value as the means to either use the recommended and default value for the treatment guidelines (value=false) or to insert the edited values into the ClinGuidelines table 340 (value=true).

H. Medical Personnel Administration Program

Figure 21:
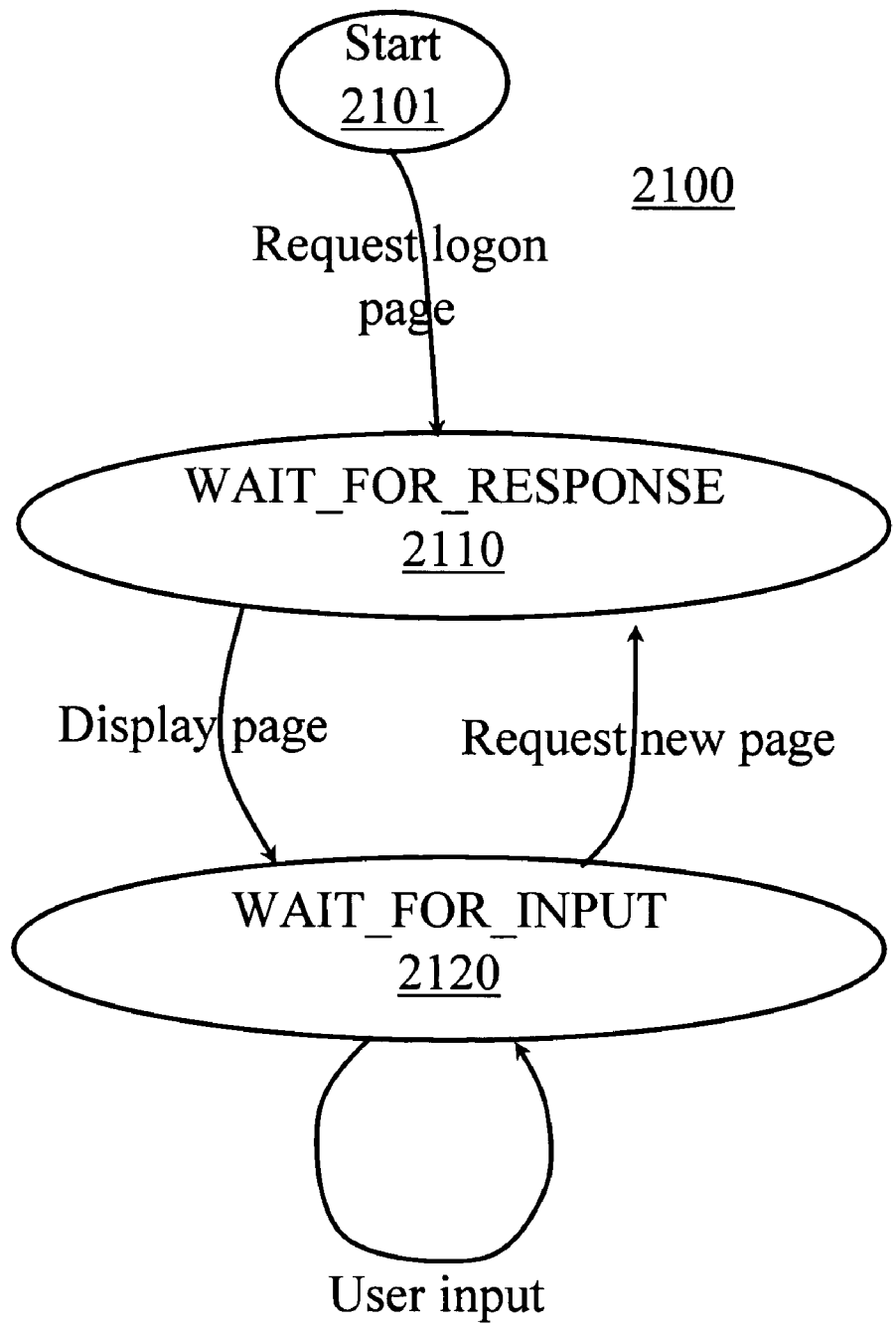
FIG. 21 is a state diagram describing the operation of the medical personnel administration program.

FIG. 21 is a state diagram 2100 showing the state machine describing the logical operation of the Medical Personnel Administration Program. Since the Medical Personnel Administration Program is operating under the Microsoft Internet Explorer Web Browser 4.0, after invocation the program is either waiting for a response from the server program or waiting for input from the user. State 'START' 2101 represents the program state when the Web Browser is started and a request is sent via http to the server program for the Medical Personnel logon page. After sending the request the program immediately transfers to the 'WAIT_FOR_RE-PONSE' 2110 state, awaiting the receipt via http of the logon html file that will display the requested page of the Medical Personnel Administration Program on the display screen of the Web Browser. When the logon file is received it is displayed or rendered by the browser on the display screen and then processing transfers to the 'WAIT_FOR_INPUT' 2120 state in which the Medical Personnel Administration Program awaits user keyboard or computer mouse input.

There are two distinct types of actions that may occur in 'WAIT_FOR_INPUT' 2120 state. The user may interact with the screen as when they use the mouse to point-and-click at a section to expand or contract it, or key enter information in one of the data entry fields displayed on the screen. This type of interaction between the user and the program results in changes to the presently displayed screen but does not cause a request to be sent to the browser for a new page. In this case the program processes the user input and remains in the state 'WAIT_FOR_INPUT' 2120.

The second type of action that may occur is when the user initiates an action, such as pressing the 'Submit' button 1307 of FIG. 13, which causes a http request message to be sent to the server requesting a new page. In this case the message is sent and the program transfers to the state 'WAIT_FOR_RESPONSE', awaiting the reception of a new page. When that page is received, it is displayed on the display screen of the Web Browser and the program transfers to the state 'WAIT_FOR_INPUT' awaiting action from the user.

The state machine for the Medical Personnel Administration Program 2100 clearly shows the reliance on the Web Browser and the Web Server for the operation of this module of the system. The browser is the operational platform that displays html pages and interacts with the user. The user may initiate actions that will result in a message to the server to formulate a new html page, wait for the response from the server, and display a new page of the Medical Personnel Administration system according to the specifics of the message request.

FIG. 22 is a state table 2200 for the operation of Medical Personnel Administration Program. It has 3 states, START 2201 which corresponds to the state 2101 of FIG. 21, WAIT_FOR_RESPONSE 2210 which corresponds to the state 2110 of FIG. 21, and WAIT_FOR_INPUT 2020 which corresponds to the state 2120 of FIG. 21. The state table provides more detail on the operation of the Medical Personnel Administration Program.

When the Medical Personnel Administration Program is started it immediately enters the logical state START 2201 in which the Internet Explorer Web Browser program is started in the Startup operation 2202. The Web Browser uses the Universal Resource Locator (URL) of the Medical Personnel Administration Program to request the file with the logon screen. In this case the URL is the network resource of the Medical Personnel Data Entry ASP file and has no QueryString associated with it. After requesting the file, the program transfers to the state WAIT_FOR_RE-SPONSE 2210 and when the file is received, performs the operation 'Display web page' 2211, displays the Medical Personnel Administration program logon screen, sets the focus to the 'Logoff' button 1390 of FIG. 13, and transfers to the state 'WAIT_FOR_INPUT' 2220.

The state 'WAIT_FOR_INPUT' 2220 is the state in which the user interacts with the Patient Program and so it is in this state that most of the html/css programming is done. There are 9 different operations that the program must be capable of handling.

If the operation is to 'Expand or Collapse' a section 2221 then if the selected section is in collapsed mode then the screen is redisplayed with the selected section in expanded mode. If the selected section is in expanded mode then the screen is redisplayed in collapsed mode. In the preferred embodiment the sections are set to their respective modes by programming the DHTML onclick event to set the style property display attribute of the sections html DIV tag to 'NONE' to collapse the section and 'BLOCK' to display it.

If the operation is to 'Change focus' 2226 then the browser resets the focus to the selected field. This will most often occur with the data entry fields. For instance if the user is entering a Username into the 'Username' field 1305 of FIG. 13, then the focus of the browser has to be on this data entry field so the browser will update the 'Username' data entry field with the keyed values. If the operation is 'Key-Entry' 2227, then the key entry is appended to the values in the data entry field that has the focus. This operation is handled by the web browser and includes support for 'Backspace' and 'Del' to remove keyed characters.

If the operation is to 'Submit Logon' 2223 then the Web Browser submits a request to the server program to validate the Username and Password of the user. The Web Browser uses the Universal Resource Locator (URL) of the Medical Personnel Administration Program with the QueryString set to name-value pairs with the Username and Password. This URL request is sent to the server and the program enters the state 'WAIT_FOR_REPONSE' 2210 waiting to receive and display a new page of the Medical Personnel Administration Program. If the treatment database server program can validate the Username and Password then it will respond with a screen containing a list of all Patients seen by the Medical Personnel and all medical appointments by each patient. If the treatment database server program cannot validate the Username and Password then it will respond with the Patient Program logon screen.

If the requested operation is to 'Submit SignUp/Update' 2224 then the Web Browser submits a request to the server program to either sign-up a new medical personnel or to update the medical personnel's information in the treatment instructions database. The Web Browser uses the URL of the Medical Personnel Administration Program with the QueryString set to the name-value pairs of the 'Register/Update' section 1010 of FIG. 10. This URL request is sent to the server and the program enters the state 'WAIT_FOR_RE- SPONSE' 2210 waiting to receive and display a new page of the Medical Personnel Administration Program. If the SignUp or update is successful then they will be logged into the system, if not already logged in, and the server will respond with the same screen as after a successful 'Submit Logon' 2223.

For both the Medical Personnel 'Logon' section and the 'SignUp/Update' section there is a 'Reset' button. If the selected operation is 'Reset' 2222, then the data entry fields associated with the respective sections are cleared to their initial state with no entries.

If the requested operation is to 'Display Office Visit' 2228 then the Web Browser submits a request to the server program to display the status of the treatment information for all appointments by the selected patient. The Web Browser uses the URL of the Medical Personnel Administration Program with the QueryString set to a name-value pair containing the patient's unique PatientID. The URL is sent to the server and the program enters the state 'WAIT_FOR_RESPONSE' 2210 waiting to receive and display a page similar to of FIG. 15.

The screen button 'Back' 1580 of FIG. 15 is displayed if the Medical Personnel Administration program is displaying the treatment instruction information for a selected patient. If the selected operation is 'Back Button' 2229, then the Web Browser uses the Universal Resource Locator (URL) of the Medical Personnel Administration Program with the QueryString set to a name-value pair with the value 'back'. This URL request is sent to the server and the program enters the state 'WAIT_FOR_REPONSE' 2210 waiting to receive and display a new page of the Medical Personnel Administration Program. The program responds with the 'prior screen'; i.e. a screen containing a list of all Patients seen by the Medical Personnel and all medical appointments by each patient.

If the requested operation is 'Submit Logoff' 2225, then the Web Browser submits a request to the server program to log the Medical Personnel out of the system. The program uses the URL of the Medical Personnel Administration Program with the QueryString indicating 'Logoff'. The URL request is sent to the server and the program enters the state 'WAIT_FOR_RESPONSE' 2210 waiting to receive and display a new 'Logon' pages just as if it had transitioned from the 'Start' state 2201. This nullifies the medical personnel login and results in the redisplay of the logon screen FIG. 13.

I. Server Program

The treatment instructions database server program executes as Microsoft Active Server Pages running under the Microsoft Internet Information Server 4.0 web server. Among other things, the web server handles session management for a multiplicity of simultaneous client programs, memory management, object management, receipt and parsing of http message requests, dispatch of files to the client in response to an http request, and processing of Active Server Pages. The writing of server side Active Server pages to dynamically generate html files based on input from the user and information contained within a database is well known to those skilled in the art. The specification will therefore focus on the logic and algorithms employed to implement the server system.

Figure 23:
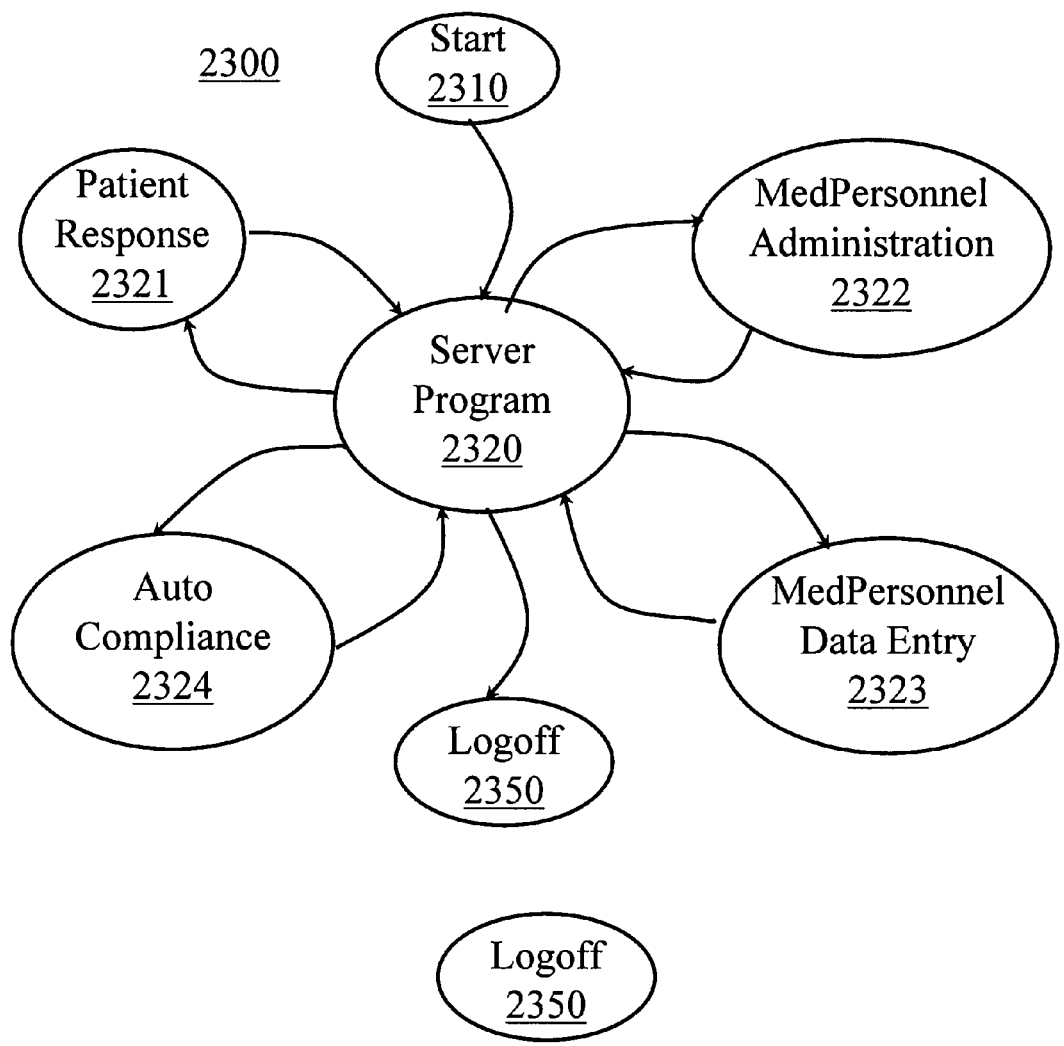
FIG. 23 is a state diagram describing the operation of the treatment instructions server program.

FIG. 23 is a state diagram 2300 for the operation of the treatment database server program. It shows the logical operation of the treatment instructions database server. At server startup 'Start' 2310 the program attempts to open the treatment instructions database. If it cannot be opened then it sends a message to the operator and immediately ends execution by transferring to the 'End' state 2380. The server program cannot run if the central treatment instructions database is not available. If the database is available then the server application program is started and the program transfers to the 'Wait for Request' state 2320, and waits for service requests from the client or to examine patients compliance and send reminders to non-compliant patients.

Logically, there are three different types of client service requests that the server program may receive, one each from the three different client programs. While service requests from different clients may be handled very similarly, for clarity in the specification, the requests are categorized by the client program that forwarded the service request to the server. If the service request is from the patient program then the server processes the request in the 'Patient Response' state 2330. If the service request is from the Medical Personnel Data Entry Program then the server processes the request in the 'MedPersonnel Data Entry' state 2340. If the service request is from the Medical Personnel Administration Program then the server processes the request in the 'MedPersonnel Administration' state 2350. In each case when a service request message is received, the program transfers to the appropriate state, parses the message, processes the response and constructs the appropriate html response file, and passes the file back to the web server to send on to the client.

Periodically, the treatment server program initiates execution of a compliance calculation and reminders program. The purpose of this program is to calculate compliance for each patient and for each patient session, store the calculated compliance in the database and send reminder messages to non-compliant patients. Compliance is calculated according to the definition rule of FIG. 4, in which a patient is only compliant if they have used the Patient Program to check all the treatment instructions specified by their medical practitioner, but limited to the set of medical appointments more than 1 weeks old and to treatment instructions that have the TrackIT boolean field of table PatCompliance 350 set to 'true'. In the preferred embodiment, the treatment server program initiates execution of the compliance calculation and reminders program at Sunday morning. Reminders are sent to all patients that are non-compliant according to their preferential means of contact as entered in their registration information 617 of FIG. 6. Every Sunday morning at 1 am, the server program is started and the treatment instructions database server program enters the 'Auto-Calc Compliance' state 2360, and initiates execution of the compliance calculation and reminders program. In the preferred embodiment the compliance calculation and reminders program is executed once a week and compliance only considers those appointments more than one week old and for whom the practitioner has expressly requested the patients compliance be tracked; i.e. the TrackIt field of table PatCompliance 350 is set to 'true'. These are parameterized settings and different setting can be utilized in the preferred embodiment. For instance, compliance calculation and reminder messages could be generated every evening rather than once a week.

All four states rely heavily on interaction with the treatment instruction database. In the preferred embodiment, the server accesses the database by use of the Microsoft ActiveX Data Objects component. The database may reside on the treatment server computer, or on another database server computer on the computer network. In either case it uses the Microsoft ODBC database driver to access the treatment instructions database from the server program.

The preferred embodiment of the program uses a Microsoft Access 97 database. This is a SQL compliant database and all communications between the server program and the database are through the industry standard SQL language. Programming database access using he SQL language is well known to those skilled in the art.

The operator may terminate the execution or shutdown the treatment server database program in which case the program first transfers to the state 'Logoff' 2370 to normally shut-down the database and then transfer to the state 'End' 2380 to terminate the treatment server database program.

FIG. 24 is a state table 2400 for the execution of the Treatment Instructions Database Server Program. It has 8 states, 'START' 2410 which corresponds to the state 2310 of FIG. 23; 'WAIT_FOR_RESPONSE' 2420 which corresponds to the state 2320 of FIG. 23; 'PATIENT_RESPONSE' 2430 which corresponds to the state 'Patient Response' 2330; 'MEDPERSONNEL DATA_ENTRY' 2440 which corresponds to the state 2340 of FIG. 23; 'MEDPERSONNEL ADMINISTRATION' 2450 which corresponds to the state 2350 of FIG. 23; 'AUTO-CALC COMPLIANCE' 246 which corresponds to the state 2360 of FIG. 23; 'LOGOFF' 2470 which corresponds to the state 2370 of FIG. 23, and 'END' 2480 which corresponds to state 2380 of FIG. 23. The state table provides more detail on the operation of the Treatment Instructions Database Server Program.

There is only one operation in state 'START' 2410, which is 'Startup' 2411. The purpose of this state is to start the execution of the server program. The server program cannot be started if the database is unavailable, so immediately after starting execution the first operation that is performed is to open the treatment instructions database. If the treatment instructions database cannot be opened or is otherwise unavailable, then a message is sent to the operator that the 'Database cannot be opened' and immediately transfer to the state 'END' 2480 to terminate the execution of the program. If the treatment instructions database is available and can be opened then processing transitions to the state 'WAIT_FOR_REQ' 2420 to wait for service requests from client programs.

In the state 'WAIT_FOR_REQ' 2420, the server program idles, awaiting a network service request from one of the client programs. When it receives a network request it can determine which client has made the request from the http message body. An http message from the Patient Program will reference the ASP patient program that processes the Patient program and transfer to the state 'PATIENT_RESPONSE 2430; an http message from the Medical Personnel Data Entry program will reference the ASP program that processes the Medical Personnel Data Entry Program and transfer to the state 'MEDPERSONNEL DATA_ENTRY' 2440, and an http message from the Medical Personnel Administration Program will reference the ASP program that processes the Medical Personnel Administration Program and transfer to the state 'MEDPERSONNEL ADMINISTRATION' 2450.

Within any of these states the processing will follow a similar pattern. First the QueryString of the message will be parsed to identify the type of message and user input. Then the ASP program will perform operations (SELECT, UPDATE, INSERT) with the treatment instructions database based on the user input, following which the ASP program will formulate the html page as a response to the client program. The response web page will be sent to the client, and finally the server will transfer back to the state 'WAIT_FOR_REQ' 2420.

In the state that processes client requests from the Patient Program, 'PATIENT_RESPONSE' 2430, there are 6 possible operations or message requests. If the message request is to start a Patient session 'Start' 2431 then the processing will proceed by generating a response page with a Patient Logon, and Register/Update sections, sending the page to the client and then transfer to the state 'WAIT_FOR_REQ' 2420. This will only allow the patient to either register for the system or logon to the system with their registered Username and Password. If the message request is for a Patient Logon 2432 then the processing will proceed by parsing the Username and Password from the QueryString, and checking if the Username and Password are in the database table 'Patients' 305. If it is, then the user is validated, and the program inserts a record in the LoginLog table 315 recording the successful login, generates a response page with a Patient Logon, Register/Update screens and recent appointments sections. The Register/Update section will have all data fields filled in with the current information from the database. The patient is now logged onto the system will be able to view compliance information for their medical appointments.

Even though the Patient has successfully logged into the system the Logon section is still generated. This is so another Patient may log into the system without having to start up a new browser session.

If the message request is for 'SignUp' 2433, then the Patient is requesting authorization to use the system. The server parses the QueryString for all the SignUp information and inserts the information into the 'Patient' Table of the treatment instruction database. The program inserts a record in the LoginLog table 315 recording the successful login, and then generates a response page with the Patient Logon, Register/Update and Recent Appointment sections, sends the page to the client and transfers to the state 'WAIT_FOR_REQ' 2420. The 'Update' message 2434 is handled similarly. The QueryString is parsed for the Update information and the Patient table of the treatment instruction database is updated with the information. The program then generates a response page with the Patient Logon, Register/Update and Recent Appointment sections, sends the page to the client and transfers to the state 'WAIT_FOR REQ' 2420.

If the message request is for the Patient's recent appointments 2435 then the QueryString is parsed for the patient and appointment identification information. The patient, appointment, diagnosis, medical personnel, and patient compliance information are retrieved from the treatment instruction database and a response page is generated with sections for the Patient Logon, Register/Update, Recent Physician Appointments, and for the selected appointments treatment instructions, alerts, followup, diagnosis and treatment information. Before the page is returned to the client the 'date-Accessed' field of the PatCompliance table of the treatment instructions database is updated with current date for each of the compliance records for the requested medical encounter. The page is then sent to the client and processing continues in the state 'WAIT_FOR_REQ' 2420. If the message request is to 'Logoff' 2436 then the processing will proceed by generating a response page with a Patient Logon, and Register/Update sections, sending the page to the client and then transfer to the state 'WAIT_FOR_REQ' 2420. This has the effect of nullifying the patient's logon, as they cannot again view appointment or compliance specific information until they again use the logon function of the patient program.

In the state that processes client requests from the Medical Personnel Data Entry Program, 'MEDPERSONNEL DATE_ENTRY' 2440, there are 7 possible operations or message requests. If the message request is to start a Medical Personnel Data Entry session 'Start' 2441 then the processing will proceed by generating a response page with a Logon, and Register/Update sections, and sending the page to the client and then transitioning to the state 'WAIT_FOR_REQ' 2420. If the message is a MedPersonnel Logon 2442, then the Username and Password are parsed from the QueryString and the program checks if the Medical Personnel is registered to use the system by checking the Username and Password in the MedPersonnel table 310 of the treatment instructions database. If the Username and Password are validated then processing will proceed by inserting a record in the LoginLog table 315 recording the successful login, generating a response page with a Logon, Register/Update and Identify Patients sections, sending the page to the client and then transitioning to the state 'WAIT_FOR_REQ' 2420.

If the message request is for 'SignUp' 2433, then the Medical Personnel is requesting authorization to use the system. The server parses the QueryString for all the SignUp information and inserts the information into the 'MedPersonnel' Table 310 of the treatment instruction database. The program then inserts a record in the LoginLog table 315 recording the successful login, generates a response page with the Medical Personnel Logon, Register/Update and Identify Patients sections, sends the page to the client and transfers to the state 'WAIT_FOR_REQ' 2420. The 'Update' message 2444 is handled similarly. The QueryString is parsed for the Update information and the MedPersonnel table 310 of the treatment instruction database is updated with the information. The program then generates a response page with the Medical Personnel Logon, Register/Update and Identify Patients sections, sends the page to the client and transfers to the state 'WAIT_FOR_REQ' 2420.

If the message request is a Patient Logon 2445 then the program parses the QueryString for the Username and Med-Password or PIN of the patient. The Username and PIN are validated against the Patients Table, and if valid the program generates a response page with the Medical Personnel Logon, Register/Update, Identify Patients, and Recent Physician Appointment sections. If the Username and Pin cannot be validated in the database then the program generates a response page with the Medical Personnel Logon, Register/Update, and Identify Patients sections. The generated page is then sent to the client and the program transitions to the state 'WAIT_FOR_REQ' 2420.

If the message request is a 'Save' 2446 message then this indicates that the Medical Personnel have finished entering the information for the patient. The program parses the QuerySting for all appointment-related information including appointment date, diagnosis, complaint, and patient compliance information. The program updates the database with this information. For each diagnosis and for every type of treatment instructions, 'Treatment instruction' 1251, Diagnosis information 1252, 'Treatment information' 1253, 'Followup'1254, and 'Alerts' 1255, if the 'Include' checkbox '1256' is checked then the program will insert a record into the PatCompliance table of the treatment instruction database to reflect that this is treatment information specified by the medical practitioner. If the corresponding compliance tracking checkbox is selected 1257, then the TrackIt field of the PatCompliance field will be set to the value 'Yes' so the system will automatically monitor the patients usage and send compliance messages.

For each diagnosis the QueryString has a value for the hidden HTML field Recommended. This field has a value of 'false' if the medical personnel have in anyway edited or modified the recommended treatment guideline. If the value of the field is 'true' then the practitioner has accepted and is using the recommended treatment guidelines, and the treatment instructions for the encounter, patient and diagnosis use the ClinGuidelineID key in the primary-foreign key relationship between the ClinGuidelines table 340 and the PatCompliance table 350. If the value is 'false', then the practitioner has modified the recommended treatment guidelines and the values of each step of the treatment guideline are inserted into the ClinGuidelines table 340 of the treatment instructions database, and a new value for the index key ClinGuidelineID is generated and will be used in the primary-foreign key relationship with the PatCompliance table 350.

After the database has been updated, the system generates a response page with the Medical Personnel Logon, Register/Update, and Identify Patients sections and the program transitions to the state 'WAIT_FOR_REQ' 1240. The system is now ready for the Medical personnel to process the next patients' appointment.

If the response message is 'Logoff' 2447 then the Medical Personnel is finished using the data entry program. Processing proceeds by generating a response page with the Logon and Register/Update sections. The response page is sent back to the client and the program transitions to the state 'WAIT_FOR_REQ' 2420. This has the effect of nullifying the medical personnel's login, as they must login again to the system to use any of the data entry options.

In the state that processes client requests from the Medical Personnel Administration Program, 'MEDPERSONNEL ADMINISTRATION' 2450, there are 7 possible operations or message requests. If the message request is to start a Medical Personnel Administration session 'Start' 2451 then the processing will proceed by generating a response page with a Medical Personnel Logon, and Register/Update sections, and sending the page to the client and then transfer to the state 'WAIT_FOR_REQ' 2420. If the message request is for a Medical Personnel Logon 2452 then the processing will proceed by parsing the Username and Password from the QueryString. If the Username and Password can be validated against the MedPersonnel table, then processing proceeds by inserting a record in the LoginLog table 315 recording the successful login, generating a response page with the Logon, Register/Update, and Patient sections. If the Username and Password cannot be validated then processing proceeds by generating a response page with the Logon and Register/Update sections. The response page is sent back to the client and the program transitions to the state 'WAIT_FOR_REQ' 2420. If a Patient section is generated it will have a section for every patient that has been seen by the Medical Personnel that is logged on, and each Patient section will in turn have a listing of all office visits by the patient with the medical personnel. Retrieving from the MedEncounter table 320 all appointments for each patient with the Medical Personnel that is logged onto the system generates the information in the Patient section.

If the message request is for 'SignUp' 2453, then the Medical Personnel is requesting authorization to use the system. The server parses the QueryString for all the SignUp information and inserts the information into the 'MedPersonnel' Table of the treatment instruction database. The program then inserts a record in the LoginLog table 315 recording the successful login, generates a response page with the Medical Personnel Logon, Register/Update and Patient sections, sends the page to the client and transfers to the state 'WAIT_FOR_REQ' 2420. The 'Update' message 2454 is handled similarly. The QueryString is parsed for the Update information and the MedPersonnel table of the treatment instruction database is updated with the information. The program then generates a response page with the Medical Personnel Logon, Register/Update and Patients sections, sends the page to the client and transfers to the state 'WAIT_FOR_REQ' 2420.

If the message request if to 'Get Office Visit 2455 then the Medical Personnel has requested to see the details of the compliance information for the patient. The QueryString is parsed for the identifier of the patient, and a response page is generated with Logon, Register/Update, and Patient sections. The patient section has subsections for each office visit, and each office visit has sections for each diagnosis. In this case the Patient section only has information for the single selected patient—not all patients as in the prior screens. The response page is sent to the client and the program transitions to the state 'WAIT_FOR_REQ' 1240 to wait on the next message request.

If the message request is 'Back' 2456, then the Medical personnel is finished examining the detailed compliance information for a patient and the program returns to the same state displayed in FIG. 14. While medical personnel are examining the patients compliance information they may choose to instruct the system to send a compliance message to the patient. They do this by checking the 'Send Reminder' checkbox 1542 of FIG. 15. They may send reminder messages even for those treatment instructions that have not been flagged with a value of 'true' in the 'TrackIt' field of the PatCompliance Table 350. Processing proceeds by parsing the QueryString which will identify any treatment instructions that the medical personnel have requested compliance reminders be sent to the patient. If there are any then the system will invoke the procedures to send reminder messages according to the preference of the patient. For instance if the patients preference is to use Email then a MAPI component will be invoked by the server to send an Email message, similar to that in FIG. 16, to the patient. Processing continues by generating a response page with the Logon, Register/Update, and Patient sections, sending the response page to the user, and transitioning to the state 'WAIT_FOR_REQ' 2420.

If the response message is 'Logoff' 2457 then the Medical Personnel has finished using the administration program. Processing proceeds by generating a response page with the Logon and Register/Update sections. The response page is sent back to the client and the program transitions to the state 'WAIT_FOR_REQ' 2420.

A key feature of the system is its ability to identify patients that are non-compliant with treatment instructions and send them compliance reminders. This is implemented in the preferred embodiment by a server program that is executed Sunday each week at 1 am in the morning and calculates for every patient and for every patient session their measure of compliance. If a patient is non-compliant then a reminder message is sent to them.

Figure 4:
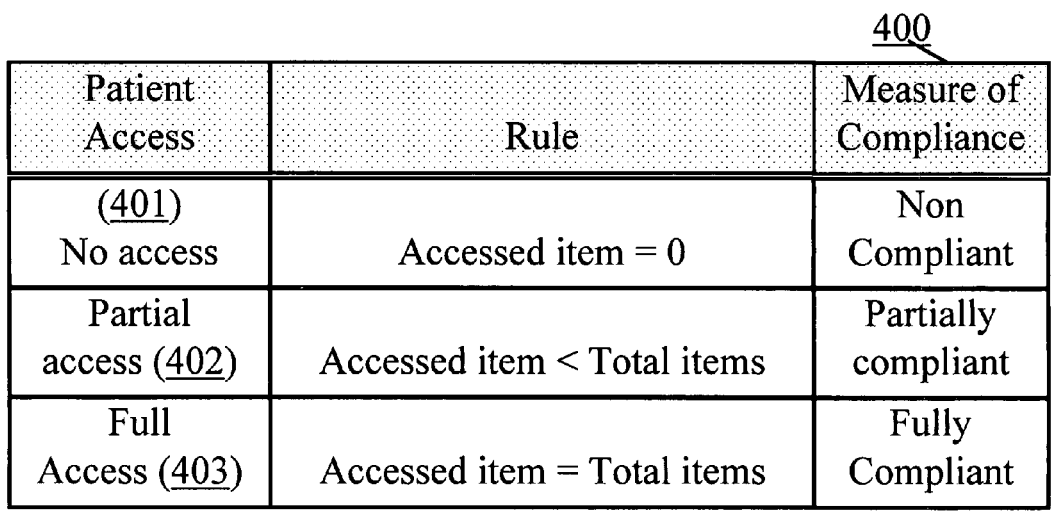
FIG. 4 is a decision matrix for assigning a measure of compliance to a patient.

When the enters the 'AUTO_CALC_COMPLIANCE' state 2460, it performs a sequence of steps to calculate compliance according to the algorithm depicted in FIG. 4, and for non-compliant patients send reminder messages. Processing proceeds by first calculating according to the algorithm described in FIG. 4, and storing a measure of compliance for each appointment more than 2 weeks old and for each patient. The compliance measure is stored in the database in the MeasCompliance field for MedEncounter. Next a compliance measure is calculated for each patient in the database. This is done by considering only those appointments in the database more than 1 weeks old and calculating according to the algorithm described in FIG. 4 a measure of compliance and then updating the MeasCompliance field of the Patients Table with the value. The last step is to retrieve from the database the calculated measure of compliance for each patient and for those that are non-compliant sending them a reminder message, by means of their preferred means of contact, as stored in the PrefMeansContact field of the Patients Table. Compliance messages are only sent if there are items in the PatCompliance table with the field 'TrackIt' set to 'true' indicating that the Medical Personnel have specifically requested the system to track the Patients compliance for the respective information and send reminder messages. After the reminder message have been processed, processing continues by transitioning to the state 'WAIT_FOR_REQ' 2420.

In the state 'LOGOFF' 2370 there is only one operation 'CloseDB' 2371 to finish and commit all transactions to the treatment instructions database and shutdown the database in a normal fashion. After the database is closed processing transitions to the state 'End' 2380, and the execution of the treatment instruction database server program is terminated.

2. Other Embodiments

Other embodiments of the inventions use the same principles to implement a system for increasing a patient's compliance to medical care instructions. In the preferred embodiment medical compliance is measured by classifying a patients access to treatment information into one of 3 categories. In other embodiments, there may be more complicated algorithms to measure and classify patients into compliance groups. In the present embodiment, non-compliant and partially compliant patients may be reminded to follow treatment instructions. In other embodiments, a multiplicity of means may be used to remind severely non-compliant patients to follow the treatment instructions.

In the present embodiment, once a patient accesses a treatment instruction source they are not subsequently issued reminders. In another embodiment, the user may be sent a reminder message in the case that the information is updated. For instance, in the case of drug alerts, if a new alert is issued, then the system can automatically determine which users are using that drug in treatment and send the new alert to them.

In still other embodiments the messaging and prompting of non-compliant or partially compliant patients to remind them about treatment instructions may be by other means including but not limited to mail, phone, beeper, or via cable TV.

The preferred embodiment uses a simple scheme to track patient compliance. If a patient accesses the medical appointment information from the patient program then they are assumed to be compliant. In other embodiments more complicated means may be used to measure compliance. For instance we may measure the length of time that patients review a page, and rate as more compliant those patients that spend more time reviewing a page that those who spend less time reviewing a page. Also, in the preferred embodiment we do not capture the information about whether the patient has hyperlinked to recommended diagnosis and/or treatment information. In other embodiments we may capture that information and use it to calculate a patient's compliance. This could be implemented by one skilled in the art either by maintaining patient session information on the server in session specific variables, or by using hidden html fields to accumulate and store user interactions as the user views different web pages, by a combination of both, or by some other means known to those skilled in the art.

In the present embodiment the list of diagnoses is contained within a single drop-down box with diagnoses identified by major and minor English language coding. If other embodiments of the invention, standard-coding definitions of diagnoses may be utilized.

In other embodiments compliance messages will be sent not just to the patient's medical practitioner but may also be sent to a supervisor and/or medical personnel who have a responsibility for compliance followup. In the preferred embodiment compliance is calculated and messages sent once each week. In other embodiments compliance may be calculated on a different schedule, and the algorithm for sending reminders may take into account when and whether prior reminder messages have been send to the patient.

Other embodiments will be apparent to those skilled in the art from consideration of the specification and practice of the invention disclosed herein. It is intended that the specification and examples be considered as exemplary only, with a true scope of the invention being indicated by the following claims.

In the present embodiment the Email address of the medical personnel is captured but is not made available in any fashion to the patient as a means to contact the practitioner. Other embodiments could provide functionality as part of the patient program to send Email to the practitioner.

What is claimed:

1. An electronic compliance promoter for use in promoting patient compliance with treatment instructions comprising:
   a medical personnel client, wherein said medical personnel client inputs from medical personnel diagnosis and treatment information regarding a patient following a medical appointment with the patient;
   a treatment server computer, wherein said treatment server computer receives diagnosis and treatment information from said medical personnel client;
   a treatment instructions database, wherein said treatment instructions database stores the diagnosis and treatment information received from said treatment server computer; and
   a patient client, wherein said patient client accesses said treatment server computer over a network and views the diagnosis and treatment information corresponding to the patient;
   wherein said treatment server computer records patient compliance information based on access by said patient client to the diagnosis information and treatment information stored on said treatment instructions database; and
   wherein both said medical personnel client and said patient client gain access to said treatment server computer to view the recorded patient compliance information.

2. The electronic compliance promoter as set forth in claim 1, wherein said treatment server computer measures patient compliance based on the patient compliance information recorded, and issues compliance reminders in response to a determination that a patient has not been compliant.

3. The electronic compliance promoter as set forth in claim 2, wherein said treatment server computer records preference data for each patient regarding information to be received by the patient.

4. The electronic compliance promoter as set forth in claim 3, wherein said treatment server computer issues reminders to patients by transmitting a reminder message over the network via at least one of e-mail, mail, phone, beeper, and cable TV based on preference data recorded by said treatment server computer.

5. The electronic compliance promoter as set forth in claim 3, wherein said treatment server computer presents diagnosis and treatment information to said patient client over the network in accordance with a preferred language recorded in the preference data.

6. A computer system for use in monitoring compliance of patients with prescribed treatments, the computer system comprising a patient client, a medical client, a treatment server, and a treatment database all connected through a network, wherein in the computer system—
   said treatment server includes a first article of manufacture comprising a machine-readable storage medium having stored therein indicia of a plurality of machine-executable program steps of a first control program, the first control program comprising the steps of:
      receiving diagnosis and treatment information for each of a plurality of patients;
      storing the diagnosis and treatment information in said treatment database in association with respective ones of the plurality of patients; and
      retrieving and serving the diagnosis and treatment information stored in said treatment database in response to a query from said patient client;
   said patient client includes a second article of manufacture comprising a machine-readable storage medium having stored therein indicia of a plurality of machine-executable program steps of a second control program, the second control program comprising the steps of:
      issuing a query to said treatment server for diagnosis and treatment information associated with an identified patient;
      accessing over the network the diagnosis and treatment information stored in said treatment database associated with the identified patient; and
      presenting the diagnosis and treatment information to the identified patient;
   said medical client includes a third article of manufacture comprising a machine-readable storage medium having stored therein indicia of a plurality of machine-executable program steps of a third control program, the third control program comprising the steps of:
      transmitting to said treatment server diagnosis and treatment information associated with each of the plurality of patients; and
      retrieving and presenting the diagnosis and treatment information stored in said treatment database associated with selected patients;
   wherein said first control program further comprises the steps of:
      determining access of the diagnosis and treatment information by the identified patient; and
      recording compliance of the identified patient based on access by the identified patient of the diagnosis and treatment information associated with the identified patient.

7. The computer system as recited in claim 6, wherein the first control program further comprises the step of calculating a measure of compliance of the identified patient based on access of informational resources listed as part of the diagnosis and treatment information served to said patient client.

8. The computer system as recited in claim 7, wherein said calculating step in the first control program is performed by measuring a length of time that the identified patient, using said patient client, reviews information on a given informational resource.

9. The computer system as recited in claim 7, wherein said calculating step in the first control program is performed by measuring a rate at which the identified patient reviews the diagnosis and treatment information on said patient client.

10. The computer system as recited in claim 7, wherein the presenting step of the second control program comprises the step of presenting, as part of the diagnosis and treatment information, a list of resources that includes a list of resources containing information relevant to the diagnosis and treatment of the identified patient.

11. The computer system as recited in claim 10, wherein said patient client is a personal computer and the network is the Internet.

12. A method of promoting patient compliance, the method comprising the steps of:

entering patient data concerning a patient, wherein the patient data comprises diagnosis and treatment information associated with a medical appointment, wherein said entering step includes— the step of entering diagnosis information that includes: (i) identification of at least one disease; and (ii) a listing of diagnosis resources containing information on the at least one disease; and the step of entering treatment information that includes: (i) treatment instructions describing the patient's treatment regimen for each disease identified in the diagnosis information; and (ii) a listing of treatment resources containing information on the treatment regimen for the at least one disease;

receiving through a network the patient data and storing the patient data in a database;

permitting the patient to retrieve the stored diagnosis and treatment information over the network from the database;

determining the access by the patient of diagnosis and treatment information, including determining the access to the listed diagnosis and treatment resources;

storing in the database a record of compliance of the patient based on the results of said determining access step;

permitting a medical administrator over the network to view the record of compliance of the patient as stored in the database; and sending a reminder to the patient regarding compliance with the treatment instructions based on the record of compliance stored in the database.

13. The method recited in claim 12, wherein said determining access step, further includes determining access to treatment instructions associated with the patient, the method further comprising:

measuring full compliance of the patient based on access to all of the treatment instructions provided to the patient;

measuring partial compliance of the patient based on access to less than a predetermined number of the treatment instructions provided to the patient; and measuring non-compliance of the patient based on no access to the treatment instructions provided to the patient.

14. The method recited in claim 12, further comprising:

storing recommended clinical guidelines in the database, wherein the recommended clinical guidelines contain information about recommended clinical therapeutic guidelines for a diagnoses; and wherein said entering step further comprises the step of prompting medical personnel with recommended clinical guidelines for selection and inclusion in the treatment instructions entered for the patient.

15. The method recited in claim 12, wherein said entering step further comprises the step of entering alert information that includes at least one symptom that may be experienced by the patient that would require immediate medical attention, the method further comprising the steps of displaying at a patient terminal:

(i) a list of medical appointments attended by the patient and the results thereof;

(ii) treatment instructions provided by medical personnel after each medical appointment listed;

(iii) alert information;

(iv) diagnosis information; and (v) treatment information.

16. The method recited in claim 12, further comprising the steps of displaying at a medical administrator terminal:

(i) a list of patients;

(ii) for each patient listed in (i), a list of medical appointments attended by each patient;

(iii) for each medical appointment listed in (ii), a list of diseases diagnosed;

(iv) for each disease listed in (iii), a list of categories of information provided to the patient, including treatment instructions, diagnosis information, treatment information, alerts, and follow-up instructions; and (v) for each category listed in (iv), an indication as to whether the patient has accessed the information in the category.

17. The method recited in claim 12, wherein said sending a reminder step comprises the step of manually initiating by a medical administrator a reminder to a patient based on the record of compliance.

\* \* \* \* \*